(12) United States Patent
Kodandaramaiah et al.

(10) Patent No.: US 9,668,804 B2
(45) Date of Patent: Jun. 6, 2017

(54) AUTOMATED CELL PATCH CLAMPING METHOD AND APPARATUS

(71) Applicants: Suhasa Bangalore Kodandaramaiah, Somerville, MA (US); Edward Stuart Boyden, Chestnut Hill, MA (US); Crag Richard Forest, Atlanta, GA (US); Brian Yichiun Chow, Cambridge, MA (US); Giovanni Talei Franzesi, Boston, MA (US)

(72) Inventors: Suhasa Bangalore Kodandaramaiah, Somerville, MA (US); Edward Stuart Boyden, Chestnut Hill, MA (US); Crag Richard Forest, Atlanta, GA (US); Brian Yichiun Chow, Cambridge, MA (US); Giovanni Talei Franzesi, Boston, MA (US)

(73) Assignees: Massachusetts Institute of Technology, Cambridge, MA (US); Georgia Tech Research Corporation, Atlanta, GA (US)

(*) Notice: Subject to any disclaimer, the term of this patent is extended or adjusted under 35 U.S.C. 154(b) by 565 days.

(21) Appl. No.: 13/676,082

(22) Filed: Nov. 13, 2012

(65) Prior Publication Data
US 2013/0225963 A1   Aug. 29, 2013

Related U.S. Application Data

(60) Provisional application No. 61/558,841, filed on Nov. 11, 2011.

(51) Int. Cl.
A61B 5/053   (2006.01)
A61B 34/30   (2016.01)
(Continued)

(52) U.S. Cl.
CPC .......... *A61B 18/14* (2013.01); *A61B 5/04001* (2013.01); *A61B 5/0538* (2013.01);
(Continued)

(58) Field of Classification Search
CPC ........ A61B 19/2203; A61B 2019/2207; A61B 5/04001; A61B 2503/40; A61B 5/0538;
(Continued)

(56) References Cited

U.S. PATENT DOCUMENTS

2012/0027807 A1* 2/2012 Chien et al. .................. 424/400
2012/0083861 A1* 4/2012 Fried et al. ..................... 607/76

OTHER PUBLICATIONS

Mahdi Azizian, Student Member, IEEE, Rajni Patel, Fellow, IEEE, Cezar Gavrilovici and Michael Poulter, Computer-Assisted Patch Clamping, 2010 IEEE International Conference on Robotics and Automation, Anchorage Convention District, May 3-8, 2010, Anchorage, Alaska, USA, pp. 4131-4136.*

* cited by examiner

*Primary Examiner* — Sean Dougherty
(74) *Attorney, Agent, or Firm* — Norma E. Henderson

(57) ABSTRACT

In an automated methodology for carrying out in vivo cell patch clamping, a cell patch clamping device is automatically moved into position and targeted to a neuron. Neuron contact is determined by analyzing the temporal series of measured resistance levels at the cell patch clamping device as it is moved. The difference between successive resistance levels is computed and compared to a threshold, which must be exceeded for a minimum number of computations before neuron contact is assumed. Pneumatic control methods are used to achieve gigaseal formation and cell break-in, leading to whole-cell patch clamp formation. An automated robotic system capable of performing this methodology automatically performs patch clamping in vivo, automatically detecting cells by analyzing the temporal sequence of electrode
(Continued)

impedance changes. By continuously monitoring the patching process and rapidly executing actions triggered by specific measurements, the robot can rapidly find neurons in the living brain and establish recordings.

20 Claims, 23 Drawing Sheets

(51) Int. Cl.
    *A61B 18/14*     (2006.01)
    *A61B 5/00*     (2006.01)
    *A61B 5/04*     (2006.01)

(52) U.S. Cl.
    CPC ............ *A61B 5/6885* (2013.01); *A61B 34/30* (2016.02); *A61B 2503/40* (2013.01)

(58) Field of Classification Search
    CPC ........... A61B 5/6885; G01N 33/48728; G01N 33/5058
    USPC .................................................. 600/547, 554
    See application file for complete search history.

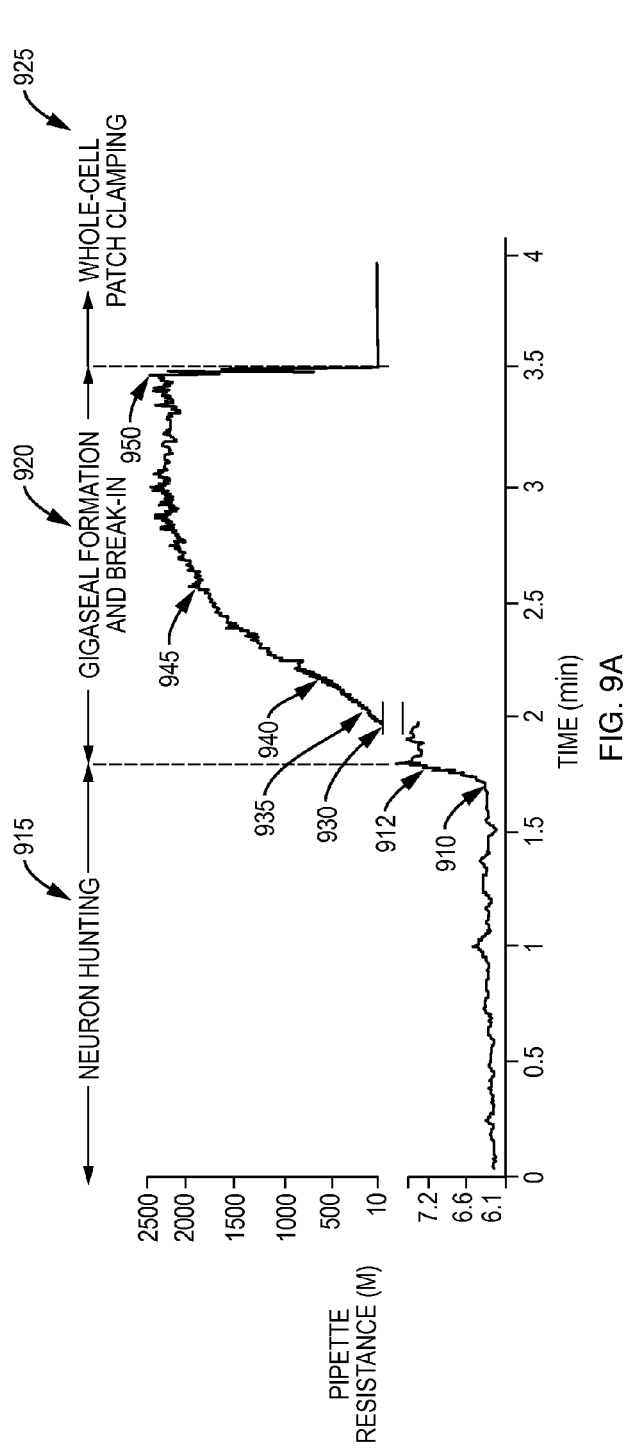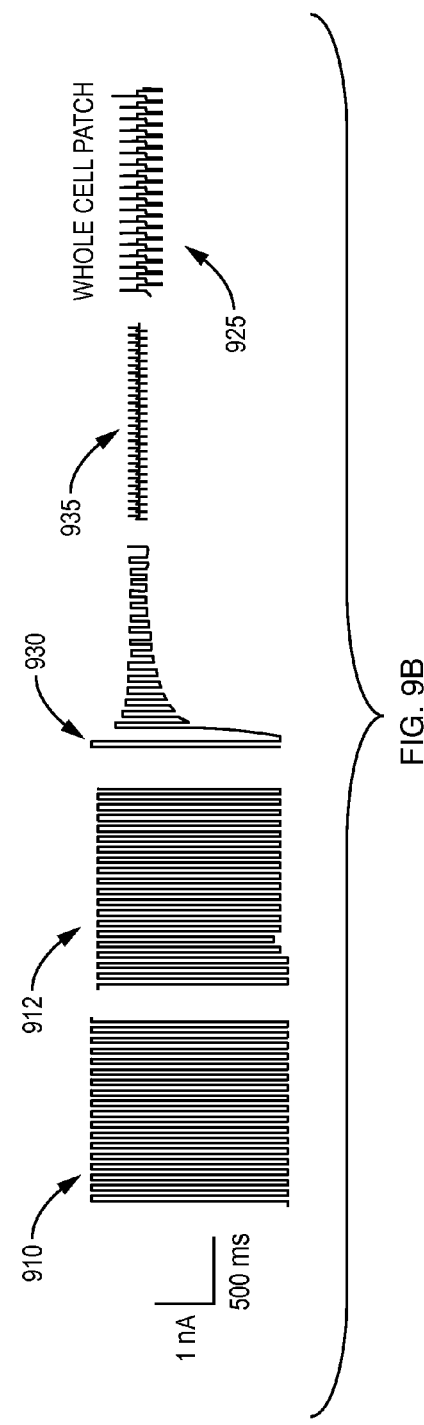

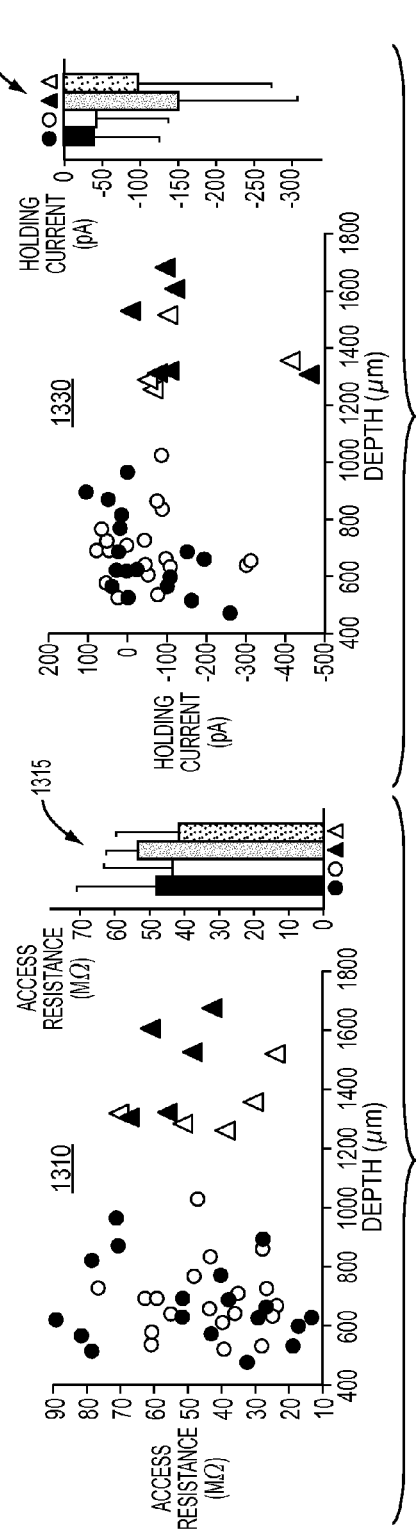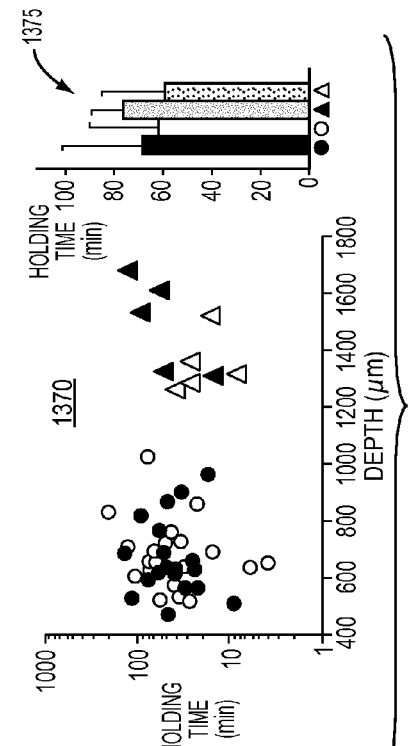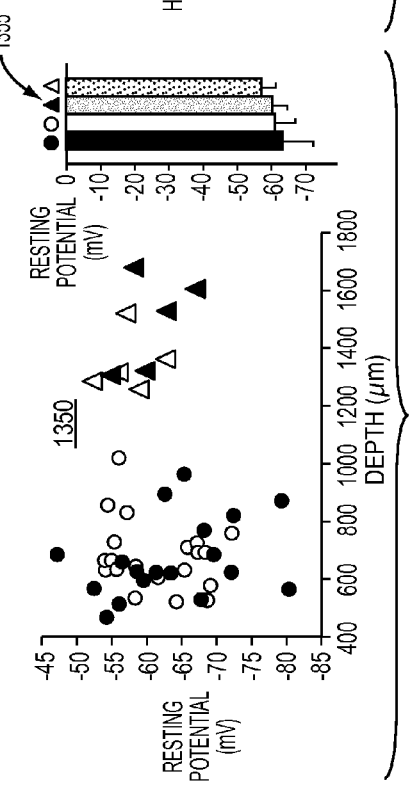
FIG. 13A
FIG. 13B
FIG. 13C
FIG. 13D

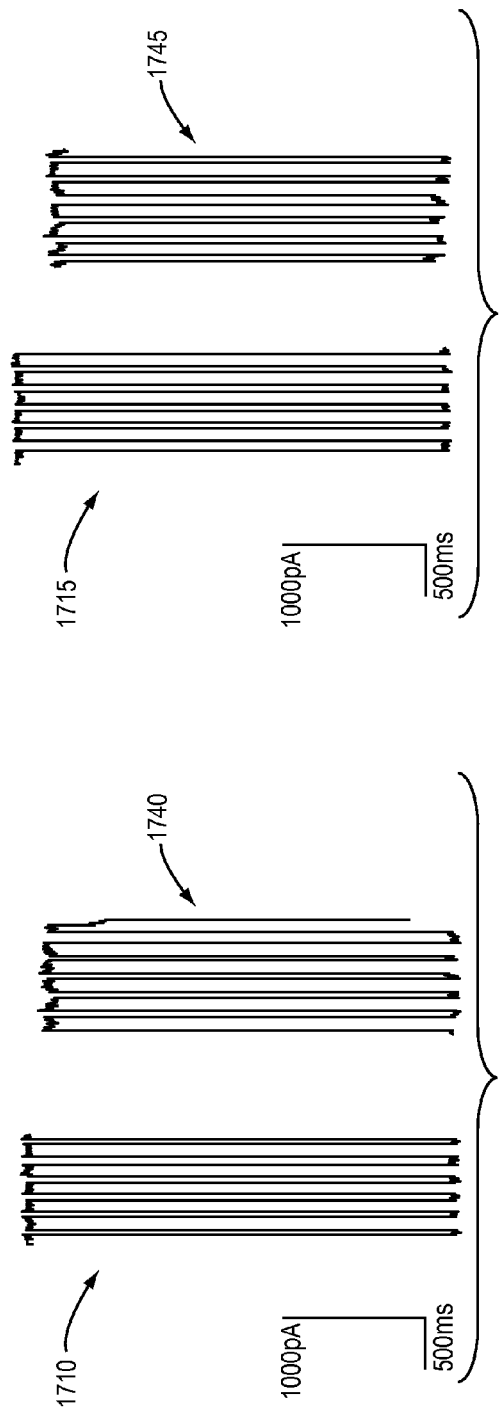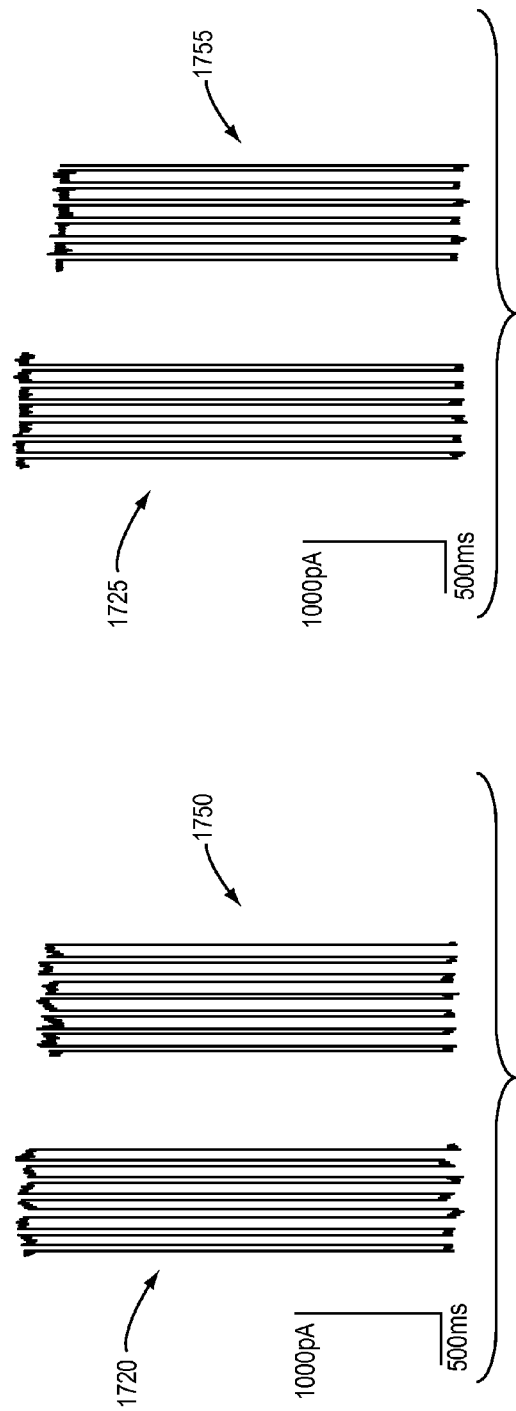

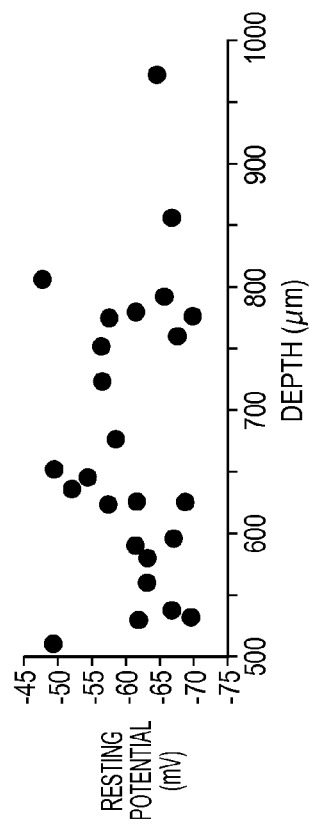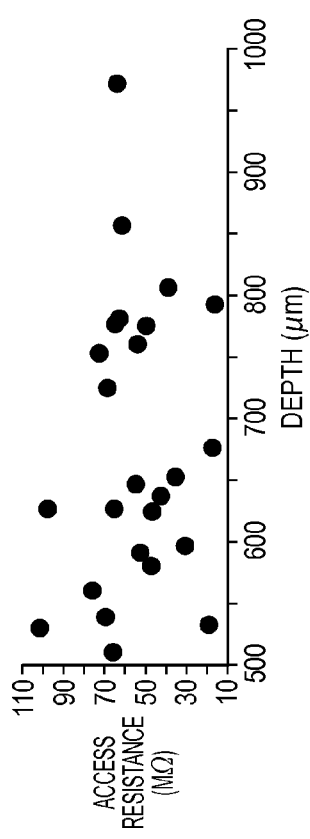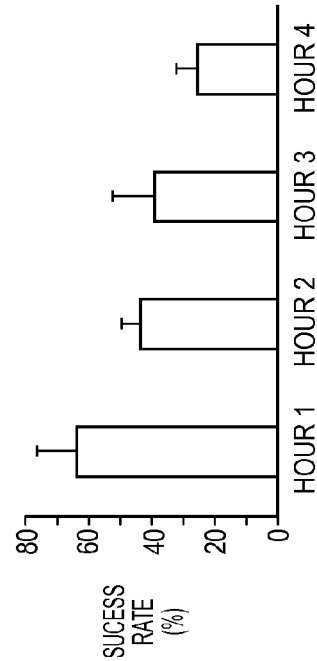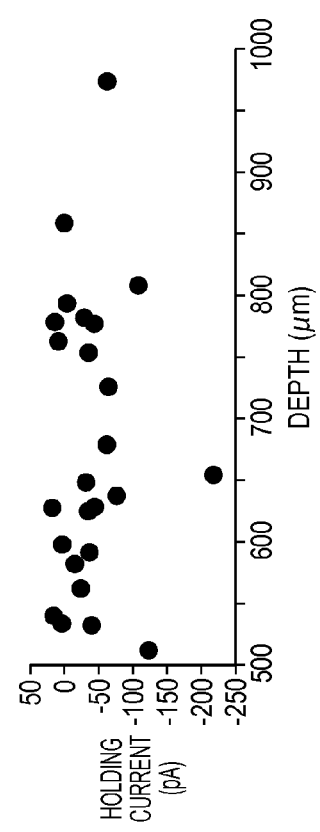

AUTOMATED CELL PATCH CLAMPING METHOD AND APPARATUS

RELATED APPLICATIONS

This application claims the benefit of U.S. Provisional Application Ser. No. 61/558,841, filed Nov. 11, 2011, the entire disclosure of which is herein incorporated by reference.

STATEMENT REGARDING FEDERALLY SPONSORED RESEARCH OR DEVELOPMENT

This invention was made with U.S. government support under Grant Numbers OD002002, EY023173, NS075421 and NS067199, awarded by National Institutes for Health and under Grant Number EFRI0835878, awarded by the National Science Foundation. The government has certain rights in this invention.

FIELD OF THE TECHNOLOGY

The present invention relates to whole-cell patch clamp electrophysiology and, in particular, to an automated in vivo whole-cell patch clamp apparatus and method.

BACKGROUND

Whole-cell patch clamp electrophysiology of neurons is a "gold standard" technique for high-fidelity analysis of the biophysical mechanisms of neural computation and pathology. Whole-cell patch clamp electrophysiology of neurons in vivo enables the recording of electrical events in cells with great precision and supports a wide diversity of morphological and molecular analysis experiments important for the understanding of single-cell and network functions in the intact brain. However, high levels of skill are required in order to perform in vivo patching, and the process is time-consuming and painstaking.

In whole-cell patch clamp electrophysiology, a glass pipette electrode is used to gain electrical and molecular access to the inside of a cell. It permits high-fidelity recording of electrical activity in neurons embedded within intact tissue, such as in brain slices, or in vivo. Whole-cell patch clamp recordings [Hamill, O. P., Marty, A., Neher, E., Sakmann, B. & Sigworth, F. J. Improved patch-clamp techniques for high-resolution current recording from cells and cell-free membrane patches. *Pflugers Arch* 391, 85-100 (1981); Margrie, T. W., Brecht, M. & Sakmann, B. In vivo, low-resistance, whole-cell recordings from neurons in the anaesthetized and awake mammalian brain. *Pflugers Arch* 444, 491-498 (2002)] of the electrical activity of neurons in vivo, which utilize the glass micropipettes to establish electrical and molecular access to the insides of neurons embedded in intact tissue, exhibit signal quality and temporal fidelity sufficient to report synaptic and ion-channel mediated subthreshold events of importance for understanding how neurons compute, and how their physiology can be modulated by brain disorders or pharmaceuticals. In vivo patching of cells in intact brain presents several capabilities that make it of great use: the recordings present extremely high signal-to-noise ratios and thus can be used to reveal subthreshold responses such as synaptic or ion channel events. Current can be delivered into a pipette to drive or silence the cell being recorded, or to support the characterization of specific receptors or channels in the cell.

Whole-cell patch clamping of cells in intact tissue also allows for infusion of chemicals and the extraction of cell contents. Molecular access to the cell enables infusion of dyes for morphological visualization, as well as extraction of cell contents for transcriptomic single-cell analysis [Eberwine, J. et al. Analysis of gene expression in single live neurons. *Proc Natl Acad Sci USA* 89, 3010-3014 (1992)], thus enabling integrative analysis of molecular, anatomical, and electrophysiological information about single neurons in intact tissue.

However, whole-cell patch clamping of cells in intact tissue is laborious, being something of an art to perform, especially in vivo. Although protocols exist for performing whole-cell patch clamp recording in such conditions, much practice is required by individual investigators to master the technique, since each step in the process of looking for a neuron and establishing the recording requires intuition as well as fast judgment and action. This has limited adoption in neuroscience to a small number of labs, and also precludes systematic or scalable in vivo patch clamping experiments.

SUMMARY

In one aspect, the present invention is a simple robot that automatically performs patch clamping in vivo, algorithmically detecting cells by analyzing the temporal sequence of electrode impedance changes. It demonstrates good yield, throughput, and quality of recording in mouse cortex and hippocampus. In another aspect, the present invention is a straightforward automated methodology for carrying out in vivo patch clamping, and an automated robotic system capable of performing this methodology. By continuously monitoring the patching process and rapidly executing actions triggered by specific measurements, the robot can rapidly find neurons in the living brain and establish recordings. The performance of the robot has been validated in both the cortex and hippocampus of anesthetized mice. The robot achieves yields, cell recording qualities, and operational speeds that are comparable to, or exceed, those of experienced human investigators. This "autopatcher" robot not only makes broadly accessible a high-performance physiological technique, but also enables systematic assessments of single cells within neural circuits. It also provides a powerful new platform for performing single-cell analyses in other kinds of intact tissue, both natural and engineered.

In one aspect, the present invention is therefore a method for automated whole-cell patch clamping using an automated apparatus for cell patch clamping. The method includes the steps of regionally localizing a recording electrode of a cell patch clamping device by causing the tip of the recording electrode to be lowered to an appropriate depth for neuron hunting, iteratively lowering the tip of the recording electrode by a small amount, measuring the resistance at the recording electrode tip after each iteration of the step of lowering, determining whether or not a target neuron has been encountered by constructing a temporal series of the resistance measurements after each iteration of the steps of lowering and measuring, iteratively continuing the steps of lowering, measuring, and determining until the temporal series of resistance measurements indicates monotonic increases in resistance over a threshold number of consecutive iterations and the increase in resistance over this measured temporal series is above a pre-set neuron detection threshold, stopping the motion of the recording electrode, initiating gigaseal formation, assessing whether or not gigaseal formation has been achieved, initiating break-in and formation of a whole-cell patch clamp if gigaseal formation has been achieved, and verifying formation of the whole-cell patch clamp.

The method may also include the step of forming a gigaseal-attached patch after gigaseal formation has been achieved and verified. The method may also include the step of providing strong positive pressure to the cell patch clamping device during the step of regionally localizing. The method of may also include, after completing the step of regionally localizing, the steps of reducing the pressure provided to the cell patch clamping device to low positive pressure, measuring the resistance at the recording electrode tip, assessing whether or not the measured resistance has increased over the set tip blockage threshold, and retracting the cell patch clamping device to indicate tip blockage and failure if the measured resistance has increased over the set tip blockage threshold. The step of initiating gigaseal formation may also include the step of releasing the positive pressure applied to the cell patch clamping device. The method may also include, after the step of assessing, the steps of applying suction pressure to the cell patch clamping device if gigaseal formation has not been achieved and then re-assessing whether or not gigaseal formation has been achieved. The step of initiating break-in and formation further may further include applying at least one of suction and an electrical pulse to the cell patch clamping device. The method may also include the step of retracting the cell patch clamping device to indicate neuron location failure if a predetermined maximum level for lowering the electrode tip has been reached.

In another aspect, the invention is a method for achieving and verifying neuron contact in an automated electrophysiology device by regionally localizing a recording electrode of the electrophysiology apparatus by causing the tip of the recording electrode to be lowered to an appropriate depth for neuron hunting, iteratively lowering the tip of the recording electrode by a small amount, measuring the resistance at the recording electrode tip after each iteration of the step of lowering, determining whether or not a target neuron has been encountered by constructing a temporal series of the resistance measurements after each iteration of the steps of lowering and measuring, and iteratively continuing the steps of lowering, measuring, and determining until the temporal series of resistance measurements indicates monotonic increases in resistance over a threshold number of consecutive iterations and the increase in resistance over this measured time series is above a pre-set neuron detection threshold.

In another aspect, the present invention is an apparatus for automated cell patch clamping. The apparatus includes cell patch formation apparatus, comprising at least one cell patch clamping device with a recording electrode, a 3-axis linear actuator configured for positioning the cell patch clamping device, a patch amplifier with computer interface, a programmable linear motor configured for moving the cell patch clamping device up and down in a temporally precise fashion, and a computer interface configured for automated closed-loop control of the programmable motor based upon a temporal series of resistance measurements made at the tip of the recording electrode. The apparatus may also include an automated control system configured for causing the tip of the recording electrode to be lowered to an appropriate depth for neuron hunting, iteratively causing the tip of the recording electrode to be lowered by a small amount, measuring the resistance at the recording electrode tip after each iteration of the step of lowering, determining whether or not a target neuron has been encountered by constructing a temporal series of the resistance measurements after each iteration of the steps of lowering and measuring, iteratively continuing the steps of lowering, measuring, and determining until the temporal series of resistance measurements indicates monotonic increases in resistance over a threshold number of consecutive iterations and the increase in resistance over this measured temporal series is above a pre-set neuron detection threshold, stopping the motion of the recording electrode, initiating gigaseal formation, assessing whether or not gigaseal formation has been achieved, initiating break-in and formation of a whole-cell patch clamp if gigaseal formation has been achieved, and verifying formation of the whole-cell patch clamp. The apparatus may further include a controllable plurality of pneumatic valves configured for application of pressure and suction to the cell patch clamping device.

In yet another aspect, the invention is a method for controlling an automated cell patch clamping device. In a cell patch formation apparatus that includes at least one cell patch clamping device with a recording electrode, a 3-axis linear actuator configured for positioning the cell patch clamping device, a patch amplifier with computer interface, a programmable linear motor configured for moving the cell patch clamping device up and down in a temporally precise fashion, and a computer interface configured for closed-loop control of the programmable motor based upon sequences of resistance measurements made at the tip of the recording electrode, the method includes regionally localizing the recording electrode by causing the linear motor to lower the tip of the recording electrode to an appropriate depth for neuron hunting, causing the linear motor to iteratively lower the tip of the recording electrode by a small amount, measuring the resistance at the recording electrode tip after each iteration of the step of lowering, determining whether or not a target neuron has been encountered by constructing a temporal series of the resistance measurements after each iteration of the steps of lowering and measuring, iteratively continuing the steps of lowering, measuring, and determining until the temporal series of resistance measurements indicates monotonic increases in resistance over a threshold number of consecutive iterations and the increase in resistance over this measured temporal series is above a pre-set neuron detection threshold, causing the linear motor to stop the motion of the recording electrode, initiating gigaseal formation, assessing whether or not gigaseal formation has been achieved, if gigaseal formation has been achieved, initiating break-in and formation of a whole-cell patch clamp, and verifying formation of the whole-cell patch clamp.

The cell patch formation apparatus may further include a controllable plurality of pneumatic valves configured for application of pressure and suction to the cell patch clamping device and the method may further include providing strong positive pressure from the controllable plurality of pneumatic valves to the cell patch clamping device during the step of regionally localizing, reducing the pressure provided to the cell patch clamping device to low positive pressure after completing the step of regionally localizing, measuring the resistance at the recording electrode tip; assessing whether or not the measured resistance has increased over the set tip blockage threshold, retracting the cell patch clamping device to indicate tip blockage and failure if the measured resistance has increased over the set tip blockage threshold, releasing the positive pressure applied to the cell patch clamping device during the step of initiating gigaseal formation, applying suction pressure from the controllable plurality of pneumatic valves to the cell patch clamping device if gigaseal formation has not been achieved, re-assessing whether or not gigaseal formation has been achieved, and initiating break-in and cell patch clamp formation by applying suction pressure from the controllable plurality of pneumatic valves and/or an electrical pulse to the cell patch clamping device.

BRIEF DESCRIPTION OF THE DRAWINGS

Other aspects, advantages and novel features of the invention will become more apparent from the following detailed description of the invention when considered in conjunction with the accompanying drawings wherein:

FIG. 9A is a plot of pipette resistance vs. time during an exemplary run of an apparatus according to the present invention;

FIG. 9B depicts the raw current traces resulting from the continuously applied voltage pulses, from which the pipette resistances of FIG. 9A were derived;

FIGS. 13A-D are exemplary plots depicting the quality of autopatched in vivo neural whole cell recordings made utilizing the prototype embodiment, including plots of access resistances obtained versus pipette depth and bar graph summaries of access resistances;

FIG. 15 depicts histograms summarizing the whole-cell patch clamp properties of the automatically whole-cell patched neurons for which recordings were automatically established in gigaseal state followed by manual break-in;

FIG. 17A-D depict raw current traces recorded during the "neuron hunting" stage using an exemplary embodiment of the invention;

FIGS. 18A-H present results obtained using the autopatcher using the 'suction pulses' embodiment of FIG. 6 for break-in and achieving the whole cell state;

DETAILED DESCRIPTION

Figure 1:
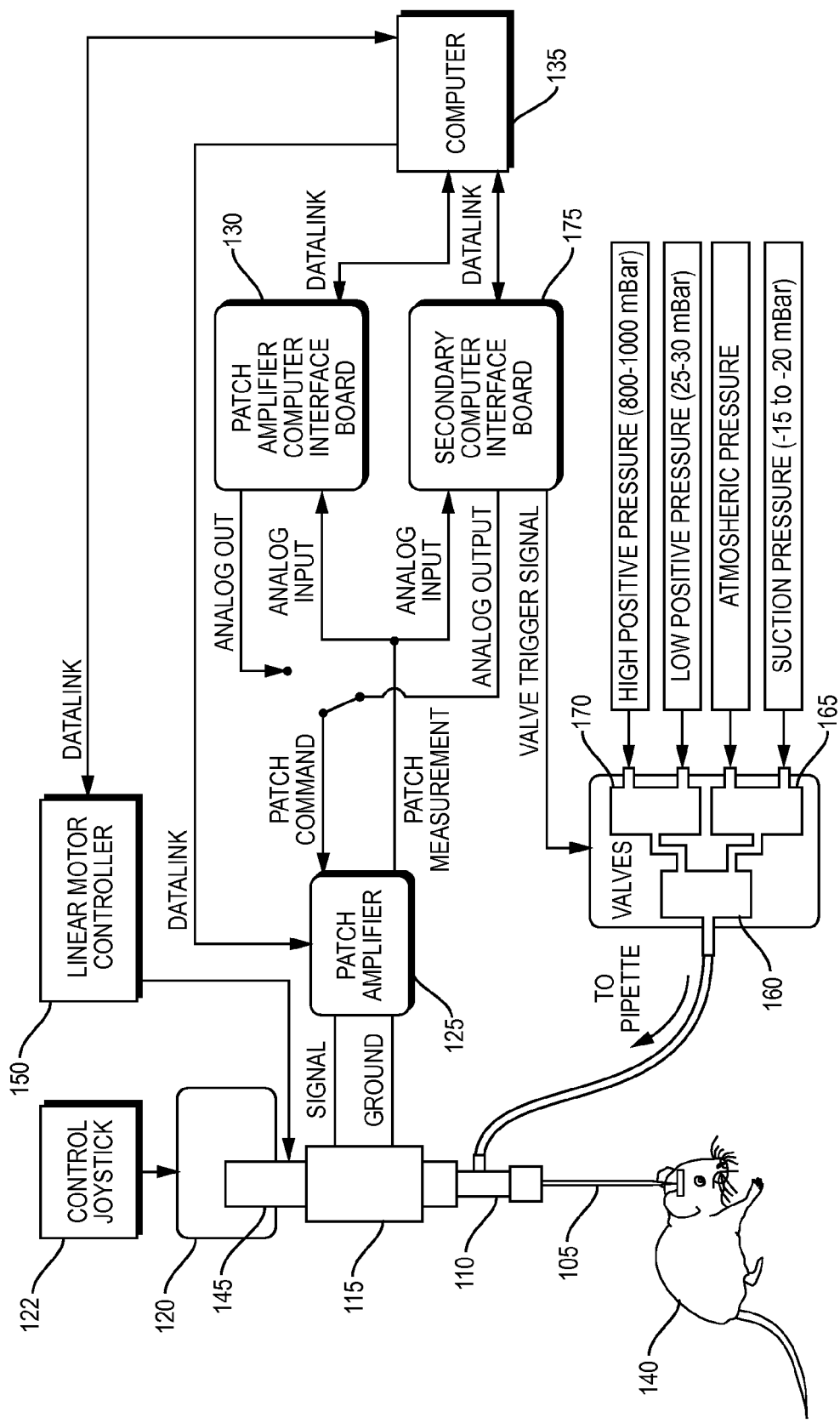
FIG. 1 is a schematic depiction of a preferred embodiment of an apparatus according to, and for carrying out, the present invention.

In one aspect, the present invention is a methodology that is executed by a robotic system in order to enable automated whole-cell patch clamp neural recording in vivo. The "autopatching" robot of the invention greatly increases throughput, opening up patch clamp technology to a greater user base within neuroscience. Additionally, the scalability and parallelizability enabled by an automated in vivo patching system according to the invention supports novel kinds of experiments, such as the use of such an autopatcher to systematically profile many individual cells for electrophysiological and molecular characterization in a brain disorder model, or the ability to perform novel kinds of pharmaceutical assessments that examine the impact of drugs on many individual cells in the context of the intact brain. It also opens up the ability to perform systematic single-cell analyses in intact tissue in other areas of bioengineering, biotechnology, and medicine, where the low throughput of, and high skill required for, patch clamping cells within intact tissues have remained barriers to adoption.

In order to derive an automated algorithm for patch clamping, each of the actions and decisions that humans perform during the process of patch clamping cells in intact tissue was assessed. Focus was placed on blind whole-cell patch clamp recording in vivo, because of its relative inexpensiveness, its usefulness in a diversity of brain regions (and not just in surface structures visualizable by optical microscopy), and its widespread utility in performing unbiased neural recordings in a diversity of species. The invention demonstrates that a simple robot comprising a programmable linear motor and a bank of pneumatic valves is capable of identifying candidate cells to record from, and establishing quality recordings of neurons in vivo, when programmed to monitor the pipette for precise sequences of changes in electrical resistance, and to actuate the motors and valves rapidly upon recognition of these changes. The precision measurement and actuation of this autopatching robot is essential for performance of the methodology of the invention, as it requires quantitative measurement and analysis, as well as fast reaction times.

The utility of the autopatching robot and methodology of the invention was demonstrated by obtaining recordings in both the cortex and hippocampus of the anesthetized mouse brain. The autopatcher was capable of achieving high yields of both whole-cell patch and gigaseal cell-attached patch recordings (~30% of overall attempts, even in deep tissue, resulted in successful recordings), exceeding yields of many trained human investigators. Acquisition of high-quality recordings proceeded rapidly (taking just 3-7 minutes each), neuron recordings could be held for an hour or longer, and recording qualities were comparable to those of trained humans (e.g., access resistances in the tens of MΩ). Being a robot, its performance did not decrease over time due to declines in attention or energy. Because the robot is automated, an individual can monitor multiple rigs at once, making the number of cells recordable by a single unskilled human investigator perhaps 100 per day or greater, and thus opening up the possibility of systematic electrical and molecular analyses of single cells in intact tissue. The autopatcher is easy to implement on existing patch clamp rigs, requiring just one inexpensive motor and a signal acquisition board, as well as a few pneumatic control valves, making it a practical solution for labs interested in automating their existing rigs, or in newly adopting the use of patch clamp technology for intact tissue analysis at the single cell level.

In one aspect of the present invention, "blind" in vivo whole-cell patching of neurons, in which micropipettes are lowered until a cell is detected and then intracellularly recorded, is reduced to a reliable methodology, in which cells are detected with >90% yield, and the whole-cell state established in >40% of detected cells. This methodology is realized by a simple automated robot, which actuates a set of motors and valves rapidly upon recognition of specific temporal sequences of microelectrode impedance changes, achieving cell-attached or whole-cell patch clamp recordings in 3-7 minutes each. The robot is relatively inexpensive, and can easily be appended to an existing patch rig. The utility of this autopatching robot in obtaining high-quality recordings, which could be held for an hour or longer, in the cortex and hippocampus of anesthetized mouse brain has been demonstrated.

A schematic depiction of a preferred embodiment of an apparatus according to, and for carrying out, the present invention is shown in FIG. 1. In FIG. 1, the system consists of a conventional in vivo patch setup, including pipette 105, pipette holder 110, headstage 115, 3-axis linear actuator 120 with control joystick 122, patch amplifier 125 plus patch amplifier computer interface board 130, and computer 135, shown set up for patching on headfixed mouse 140. The robot of FIG. 1 is additionally equipped with three additional simple modules: programmable linear motor 145 with linear motor controller 150, which functions to move pipette 105 up and down in a temporally precise fashion, controllable bank 155 of pneumatic valves 160, 165, 170 for pressure control, and secondary computer interface board 175 that enables closed-loop control of motor 145 based upon sequences of pipette resistance measurements. If the vertical axis of 3-axis linear actuator 120 is computer-controlled, programmable linear motor 145 with linear motor controller 150 can be omitted, and if patch amplifier 125 plus patch amplifier computer interface board 130 provides direct access to measurements, secondary computer interface board 175 can be omitted. While specific parts and implementation details are described herein with respect to the embodiment of FIG. 1, it will be clear to one of skill in the art of the invention that many other comparable parts, software, and implementation methodologies exist and would be equally suitable for use in the present invention.

The robotic system of FIG. 1 was designed both to explore the parameterization of the in vivo patch process, and to perform the autopatching methodology. The robot of FIG. 1 monitors pipette resistance as the pipette is lowered into the brain, and automatically moves the pipette in incremental steps via the linear actuator. In one embodiment, the pipette resistance monitoring can be performed by a traditional patch amplifier and digitizer, and the 3-axis linear actuator typically used for in vivo patching can be used as the robotic actuator. For flexibility, an optional additional computer interface board was added to support pipette resistance monitoring, and an additional linear actuator for pipette movement. The robot also contains a set of valves connected to pressure reservoirs to provide positive pressure during pipette insertion into the brain, as well as negative pressure as necessary to result in gigaseal formation and attainment of the whole cell state.

The process of the robot performing whole-cell patch clamp neural recording in vivo is a multi-step process. First, high pressure is applied to the pipette to prevent pipette blockage as it enters the brain, and the pipette electrical resistance is evaluated (e.g., between 3-9 MΩ is typical). If the pipette is of acceptable resistance, it is automatically lowered to a pre-specified target region within the brain (the stage referred to as "regional pipette localization"), followed by a second critical examination of the pipette resistance for quality control. This check is followed by an iterative process of lowering the pipette by small increments, while looking for a pipette resistance change indicative of proximity to a neuron suitable for recording (the "neuron hunting" stage). During this phase, the robot looks for a specific sequence of resistance changes that indicates that a neuron is proximal, attempting to avoid false positives that would waste time and decrease cell yield. After detecting this signature, the robot halts movement, and begins to actuate suction and pipette voltage changes so as to form a high-quality seal connecting the pipette electrically to the outside of the cell membrane (the "gigaseal formation" stage), thus resulting in a gigaseal cell-attached recording. If whole-cell access is additionally desired, the robot then performs controlled application of suction as well as brief electrical pulses to break into the cell (the "break-in" stage). Throughout the process, the robot applies a voltage square wave to the pipette (10 Hz, 10 mV alternating with 0 mV relative to pipette holding voltage), and the current is measured, in order to calculate the resistance of the pipette at a given depth or stage of the process. Throughout the entire process of robot operation, this pipette resistance is the chief indicator of pipette quality, cell presence, seal quality, and recording quality, and the algorithm attempts to make decisions—such as whether to advance to the next stage, or to restart a stage, or to halt the process—entirely on the temporal trajectory taken by the pipette resistance during the experiment. The performance of the robot is enabled by two critical abilities of the robot: its ability to monitor the pipette resistance quantitatively over time, and its ability to execute actions in a temporally precise fashion upon the measured pipette resistance reaching quantitative milestones.

Figure 2:
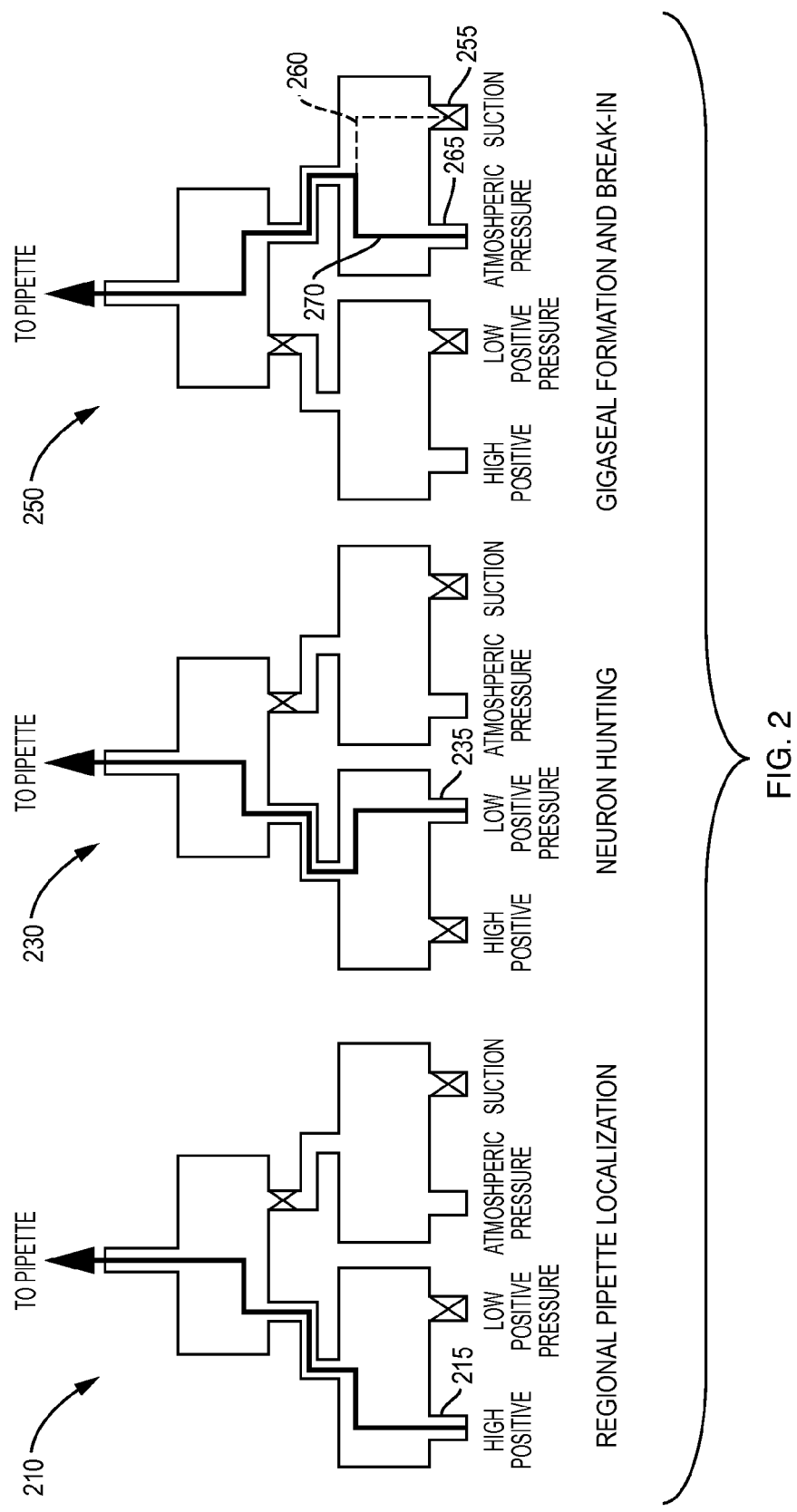
FIG. 2 is a schematic depicting exemplary configurations of the three pneumatic valve banks of FIG. 1 during the stages of Autopatcher operation, according to one aspect of the present invention.

FIG. 2 is a schematic depicting the configurations of the pneumatic valve banks of FIG. 1 during the stages of autopatcher operation. In FIG. 2, "x" represents closed valves and lines depict connectivity of volumes at the same pressure. During regional pipette localization stage 210, positive pressure 215 (800-1,000 mBar) is connected to the pipette. This is also the configuration realized when the valves are not powered. During neuron hunting stage 230, low positive pressure 235 (25-30 mBar) is connected to the pipette. During gigaseal formation stage 250, suction pressure 255 (−15 to −20 mBar; dotted line 260) or atmospheric pressure 265 (solid line 270) is applied. During the break-in stage, suction pressure 255 is also applied.

A prototype system was implemented that comprised a 3-axis linear actuator (MC1000e, Siskiyou Inc), for holding the patch headstage, and a patch amplifier (Multiclamp 700B, Molecular Devices) that connects its patch headstage to a computer through a Digidata 1440A analog/digital interface board (Molecular Devices). For programmable actuation of the pipette in the vertical direction, a programmable linear motor (PZC12, Newport) was mounted onto the 3-axis linear actuator. The headstage was in turn mounted on the programmable linear motor through a custom mounting plate. The programmable linear motor was controlled using a motor controller (PZC200, Newport Inc) that was connected to the computer through a serial COM port. An additional data acquisition (DAQ) board (USB6259, National Instruments Inc) was connected to the computer via a USB port, and to the patch amplifier through BNC cables, for control of patch pipette voltage commands, and acquisition of pipette current data, during the execution of the autopatcher algorithm. During autopatcher operation, the USB 6259 board sent commands to the patch amplifier; after acquisition of cell-attached or whole-cell-patched neurons, the patch amplifier would instead receive commands from the Digidata. The patch amplifier streamed its data to the analog input ports of both the USB DAQ and the Digidata throughout and after autopatching. For pneumatic control of pipette pressure, a set of three solenoid valves (2-input, 1-output, LHDA0533215H-A, Lee Company) was used. The autopatcher program was coded in, and run by, Labview 8.6 (National Instruments). The USB6259 DAQ sampled the patch amplifier at 30 KHz and with unity gain applied, and then filtered the signal using a moving average smoothening filter (half width, 6 samples, with triangular envelope), and the amplitude of the current pulses was measured using the peak-to-peak measurement function of Labview. During the entire procedure, a square wave of voltage was applied, 10 mV in amplitude, at 10 Hz, to the pipette via the USB6259 DAQ analog output. Resistance values were then computed, by dividing applied voltage by the peak-to-peak current observed, for 5 consecutive voltage pulses, and then these 5 values were averaged.

Figure 3:
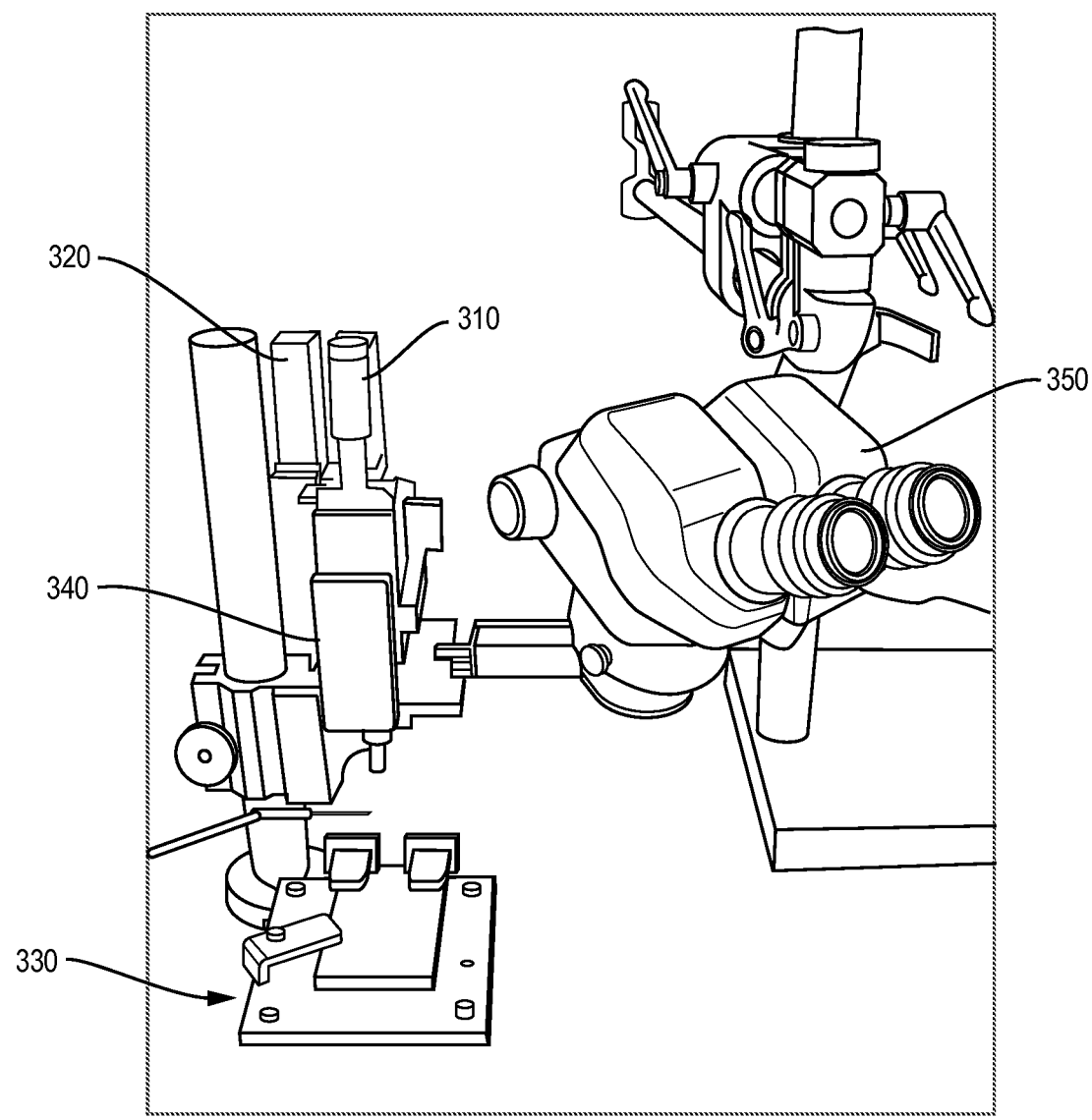
FIG. 3 depicts a prototype apparatus implemented according to one aspect of the present invention.

FIG. 3 depicts the prototype apparatus, showing programmable linear motor 310 attached to 3-axis linear actuator 320, low-profile holder 330 for head-fixing the mouse, headstage 340, and stereomicroscope 350.

The patch algorithm takes place in four stages: "regional pipette localization," in which the pipette is rapidly lowered to a desired depth under positive pressure; "neuron hunting," in which the pipette is advanced more slowly at lower pressure until a neuron is detected, as reflected by a specific temporal sequence of electrode impedance changes; "gigaseal formation," in which the pipette is hyperpolarized and suction applied to create the gigaseal; and "break-in," in which a brief voltage pulse ("zap") is applied to the cell to establish the whole cell state.

Figure 4:
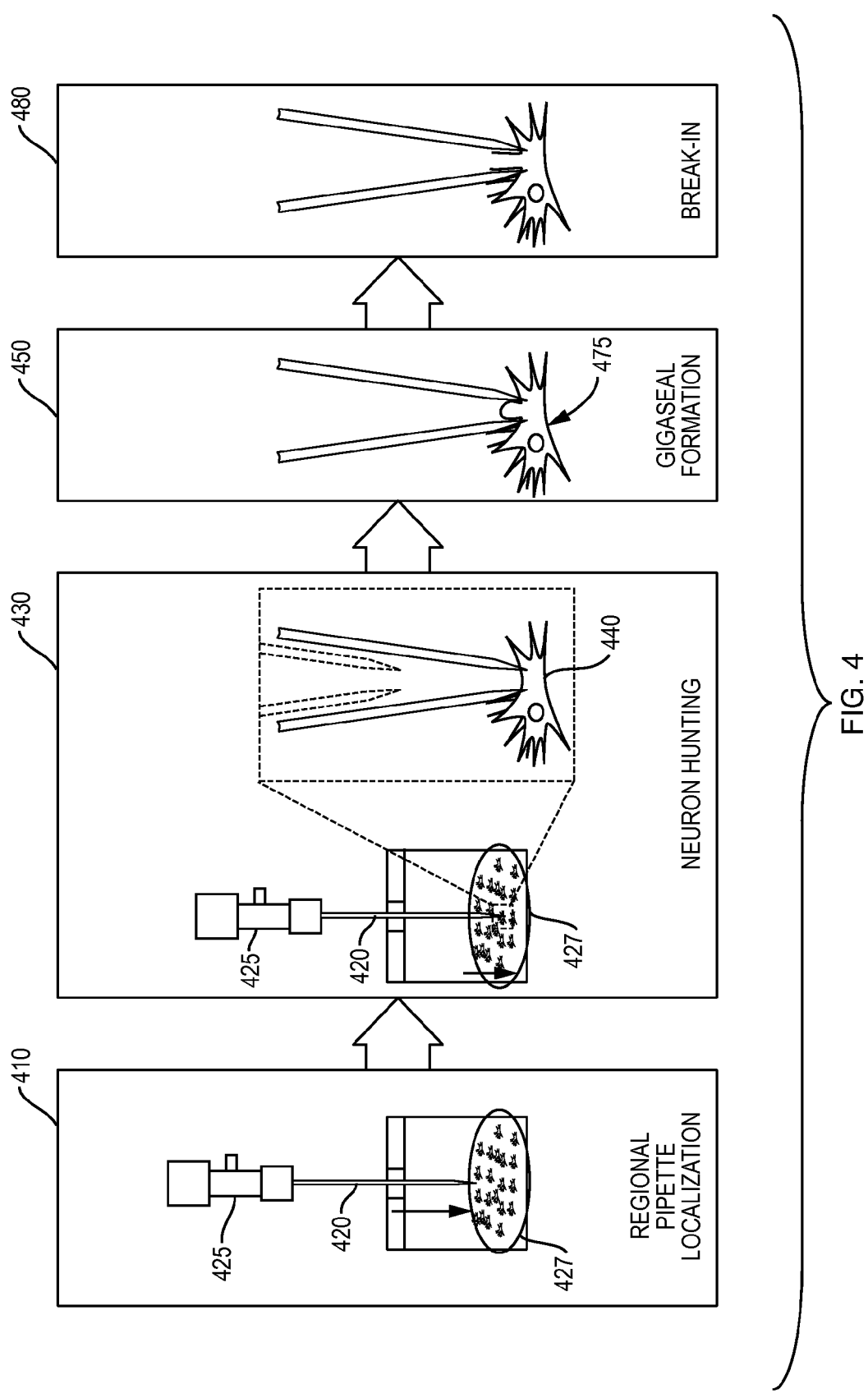
FIG. 4 is a visual depiction of the four stages of the in vivo patch process carried out using the apparatus and methodology of the present invention.

FIG. 4 depicts visually the four stages of the in vivo patch process: regional pipette localization stage 410, during which pipette 420 in holder 425 is lowered to target zone 427 in the brain; neuron hunting stage 430, during which pipette 420 is advanced until neuron 440 is detected via a change in pipette resistance; gigaseal formation stage 450, during which gigaseal cell-attached patch state 475 is achieved; and break-in stage 480, during which the whole cell configuration is achieved. For each stage, the parameters governing success of the stage were systematically explored, as well as the success of the overall procedure, resulting in the discovery of a number of stereotyped strategies appropriate for robotic execution, as well as precise numerical milestones governing within-stage and between-stage decisions, including quantitative measures of pipette quality, cell presence, and seal quality derived from the pipette resistance.

Figure 5A:
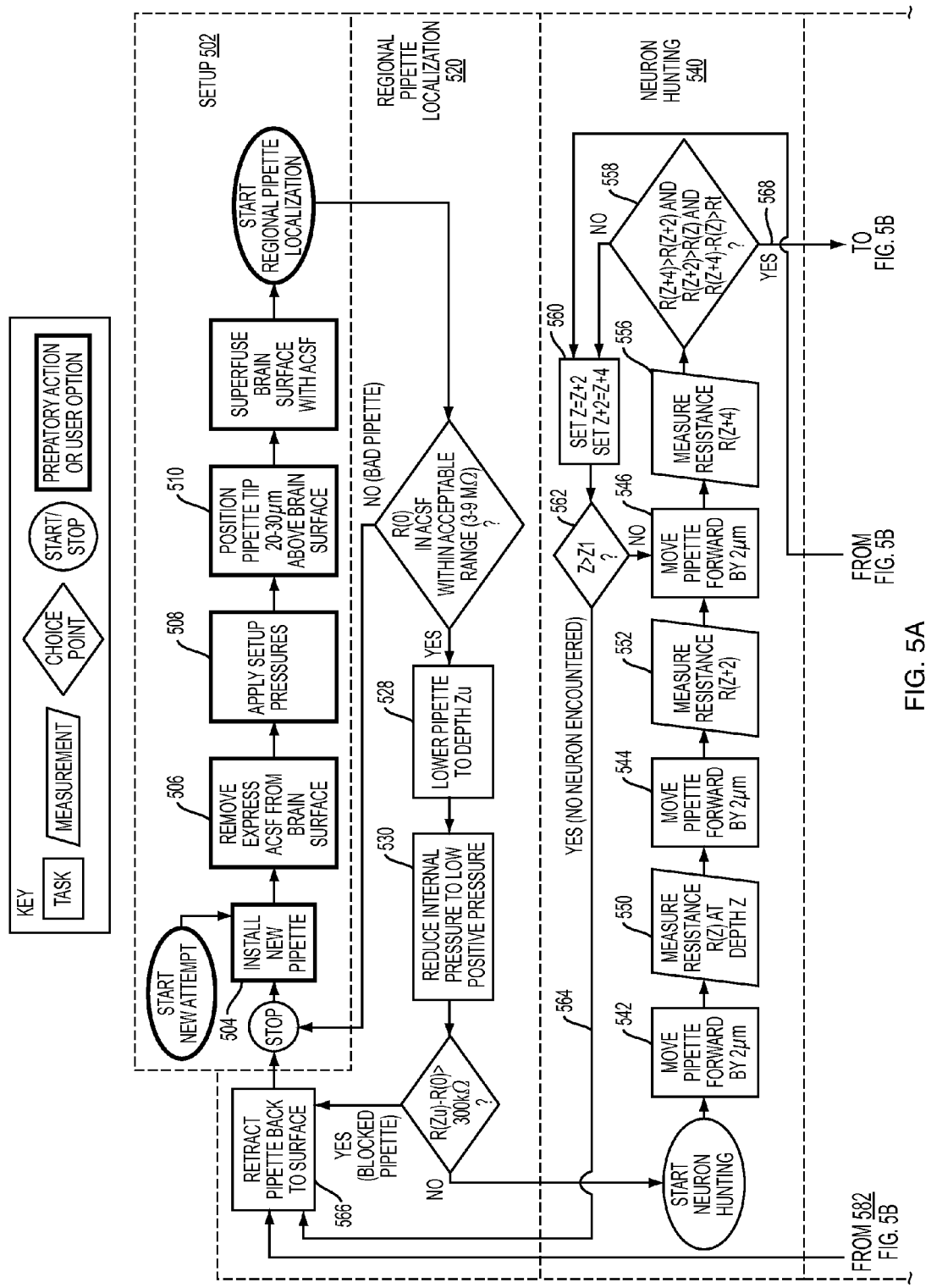
FIGS. 5A-B is a flowchart showing the steps of a preferred embodiment of the automated in vivo patch process according to one aspect of the invention, including strategies for stage execution, and quantitative milestones governing process flow and decision making.
Figure 5B:
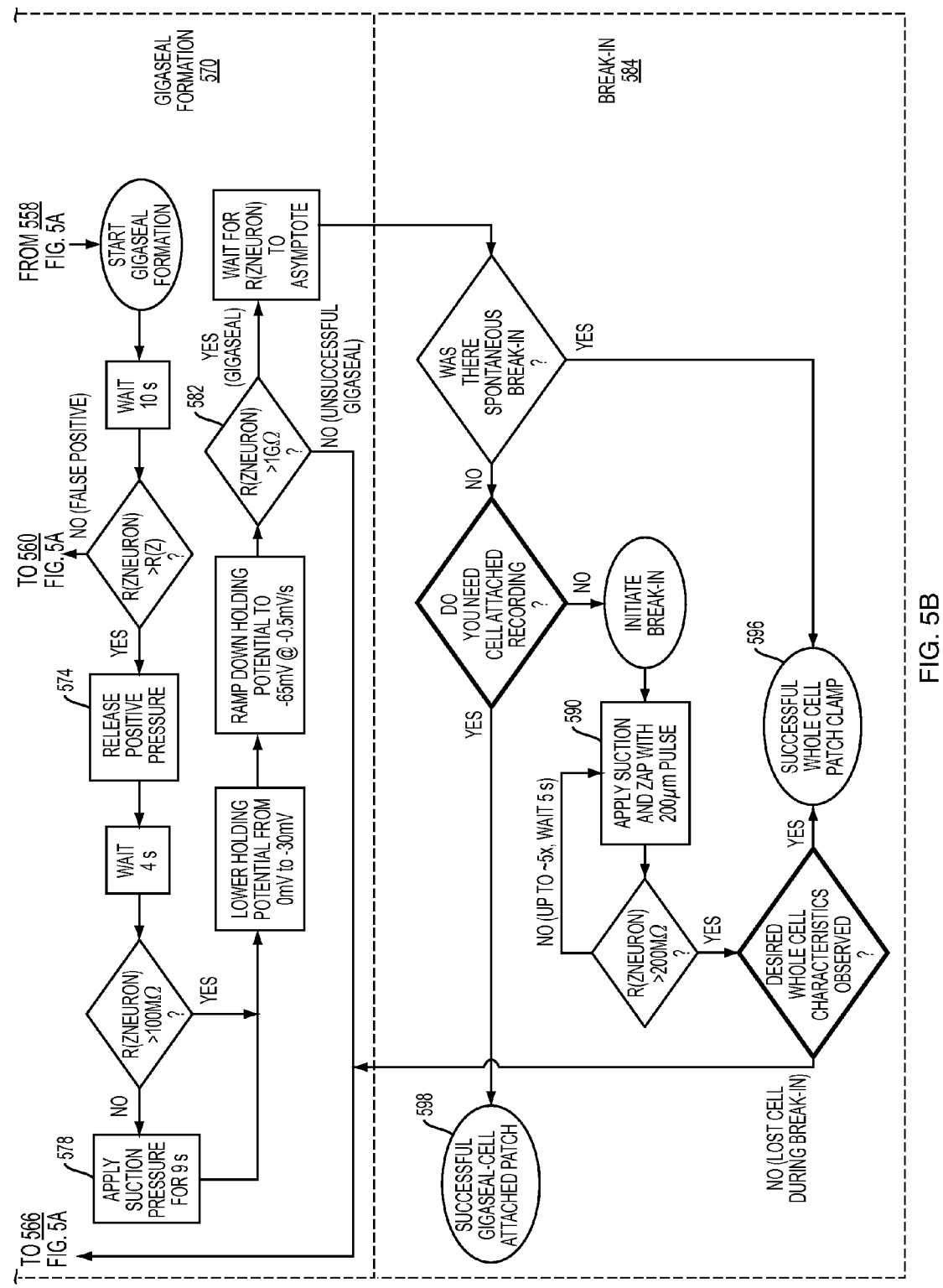

FIGS. 5A-B is a flowchart showing the steps of a preferred embodiment of the automated in vivo patch process according to one aspect of the invention, including strategies for stage execution, and quantitative milestones governing process flow and decision making. In FIGS. 5A-B, during setup stage 502, a pipette is placed 504 in the holder, excess artificial cerebrospinal fluid (ACSF) may be removed 506 from the brain surface, and strong positive pressure is provided 508 while the pipette is positioned. During regional pipette localization stage 520, the robot lowers 528 the pipette at a speed of 200 µm/s to the appropriate depth for neuron hunting and then reduces 530 the internal valve pressure to low positive pressure (see FIG. 2). During neuron hunting stage 540, the robot iteratively moves 544, 546, 548 the pipette and measures 550, 552, 554 the resistance in order to determine whether or not a neuron has been encountered. If, as determined by the time series of resistance measurements 558, no neuron has been encountered 564 after the pipette distance has been repeatedly adjusted 560 and the maximum probe depth has been reached 562, the pipette is retracted 566 back to the surface for possible installation 504 of a new pipette. If, as determined by the resistance measurements, a neuron has been encountered 568, gigaseal formation stage 570 begins, starting with release 574 of positive pressure on the pipette and, if necessary, application 578 of suction pressure. Once gigaseal formation is achieved and verified 582, break-in stage 584 begins. During break-in stage 584, break-in is initiated by application 590 of suction and a "zap" pulse, leading hopefully to a successful whole cell patch clamp 596. Alternatively, or in addition, a gigaseal-cell attached patch may be achieved 598.

Abbreviations used in the steps depicted in FIGS. 5A-B and 6A-B include: ACSF, artificial cerebrospinal fluid; R(Z), pipette resistance at depth Z in the brain, in microns (with the z-axis pointing downward, e.g. larger values of Z indicate deeper targets); Zu, upper depth limit of the region targeted by the regional pipette localization stage; Zl, lower depth limit of the region targeted by the regional pipette localization stage; R(ZNeuron), pipette resistance at the depth at which the neuron is being recorded (which will vary over time, as the later stages of the process, gigasealing and breaking-in, occur); and Rt, pipette resistance threshold for neuron detection.

A key aspect of the autopatcher automated methodology is that the robot analyzes the temporal series of the measured pipette resistances in order to determine whether a cell has been located or not. In the preferred embodiment, the robot computes the difference between successive pipette resistances and compares it to a constant threshold. This can be expressed as:

For a series of multiple consecutive pipette positions (equal or unequal in spacing), 1 to n, with r(n) being the measurement of the resistance at position n and n is greater than or equal to 2, a neuron that is suitable for patching has been encountered if:

$r(n)-r1>\text{threshold}$, where $n>1$ $r(n)>r(n-1)$

For example, a neuron suitable for patching has been encountered at position 3, if r3−r1>threshold and r3>r2>r1.

It will be clear to one of skill in the art that the execution of this algorithm would be extremely difficult, if not impossible, for humans to do manually in a rapid, systematic way. The systematic execution of such a series of steps in time (i.e., monitoring resistance, determining position, voltage, and pressure) has therefore not before been possible. Automated in vivo cell patching according to the invention works because the algorithm employed overcomes this problem and also mitigates the challenges of the noisy environment, such as heart beat, breathing, and non neuronal cells.

The autopatcher algorithm was initially derived by analyzing and optimizing successively each of the four stages of robot operation depicted in FIG. 4. The derivation of the algorithm of FIGS. 5A-B was performed completely through experiments in the cortex, but the testing of the algorithm was performed on both cortical neurons as well as hippocampal neurons. This generalization of the algorithm from cortex to hippocampus implies that the algorithm possesses a certain degree of generalization power, i.e., the algorithm was not unconsciously optimized just for one brain region. Nevertheless, it is likely that very specialized neurons in novel brain regions may require tuning of select algorithm parameters, and the ability to perform this optimization using the robot would accelerate this process of customization, allowing for rapid iteration beginning from the parameters derived here. The autopatcher was also tested on brain slices, where it was capable of obtaining good recordings.

Figure 6A:
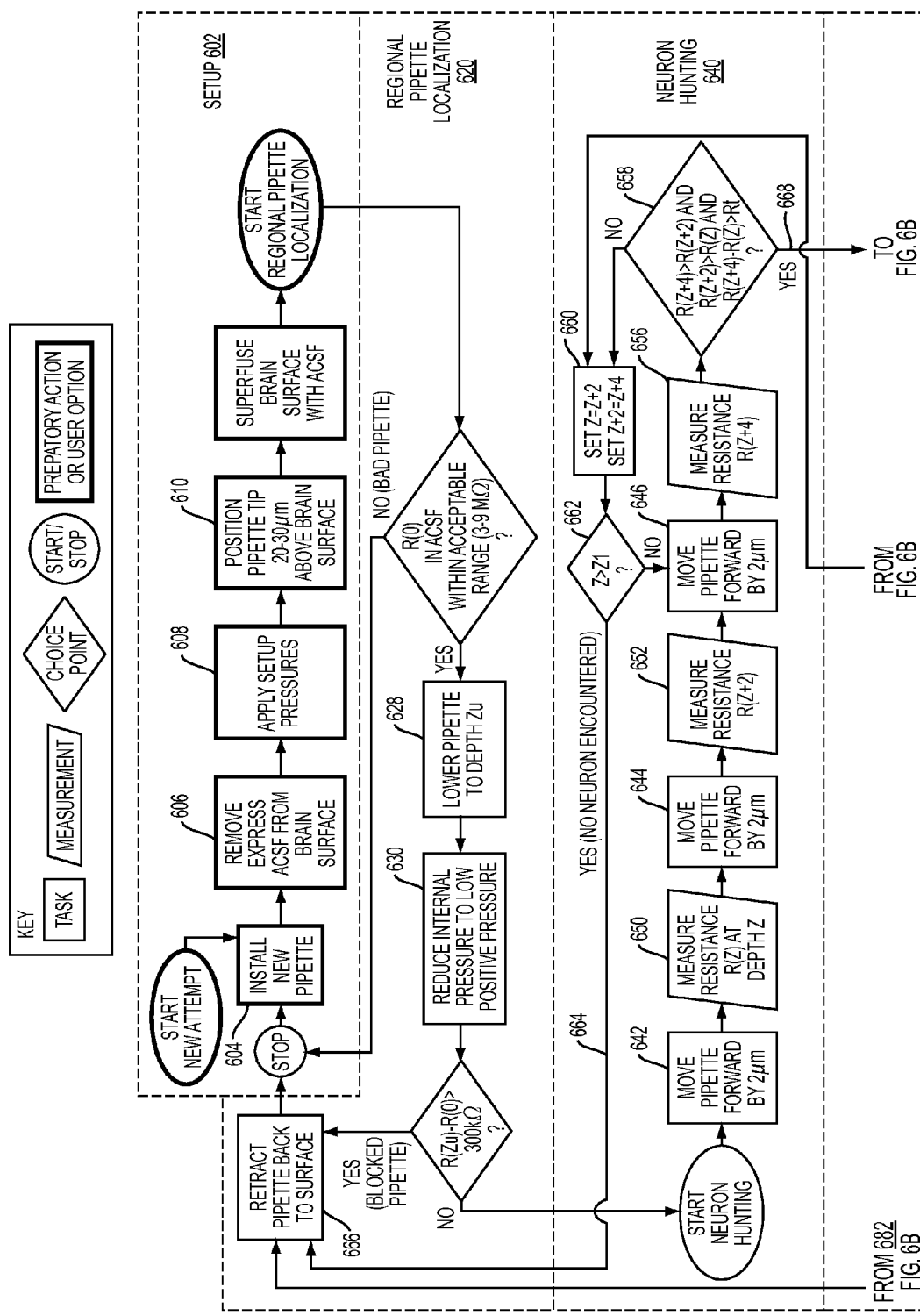
FIGS. 6A-B is a flowchart showing the steps of an alternate embodiment of the automated in vivo patch process according to one aspect of the invention.
Figure 6B:
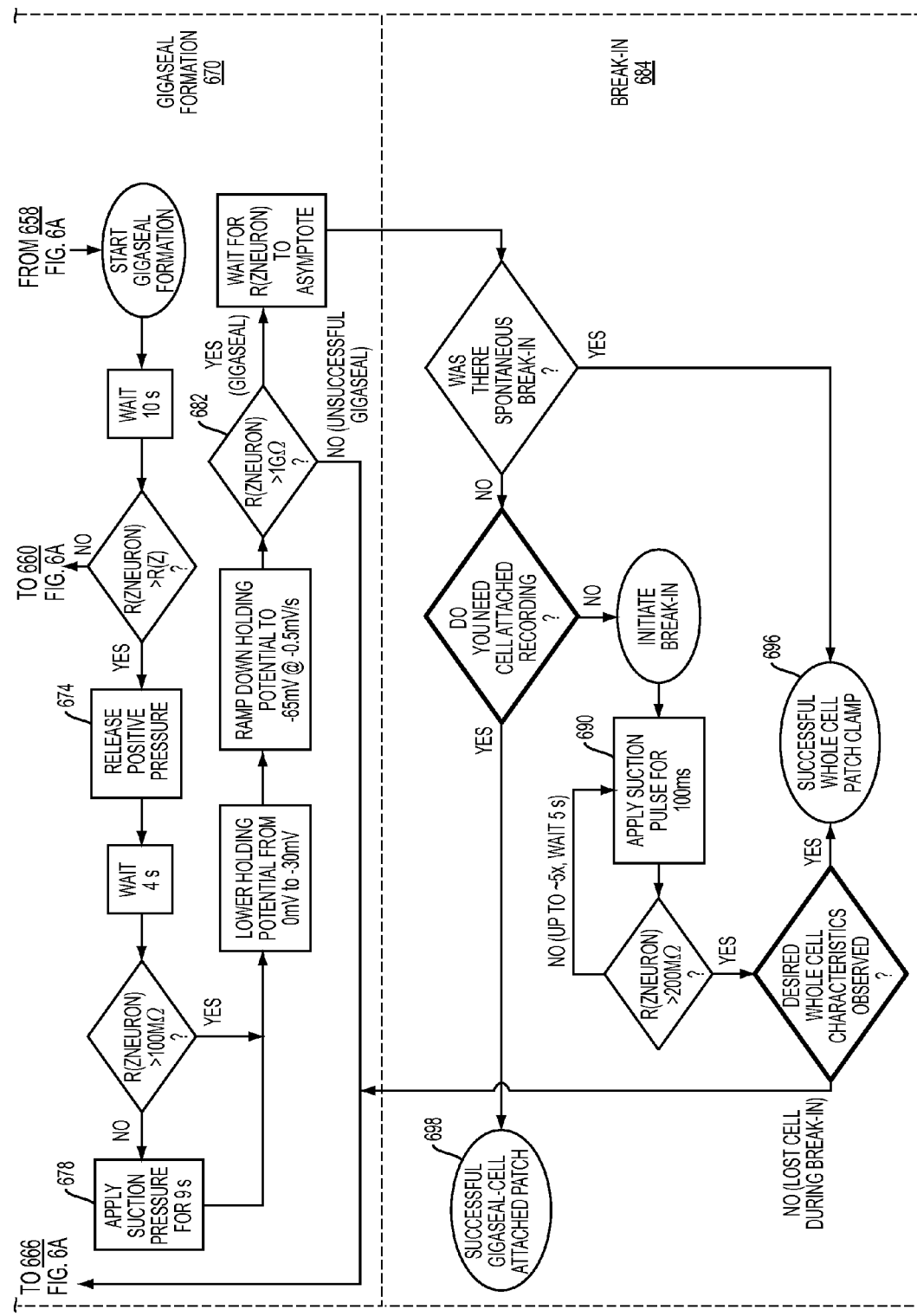

In an alternative embodiment of the methodology of the invention, shown in FIGS. 6A-B, the algorithm of FIGS. 5A-B was modified to use only suction pulses instead of suction plus "zap" pulses for the break-in stage in order to achieve a whole-cell patch clamp. As shown in FIGS. 6A-B, during setup stage 602, a pipette is placed 604 in the holder, excess artificial cerebrospinal fluid (ACSF) may be removed 606 from the brain surface, and strong positive pressure is provided 608 while the pipette is positioned. During regional pipette localization stage 620, the robot lowers 628 the pipette at a speed of 200 μm/s to the appropriate depth for neuron hunting and then reduces 630 the internal valve pressure to low positive pressure (see FIG. 2). During neuron hunting stage 640, the robot iteratively moves 644, 646, 648 the pipette and measures 650, 652, 654 the resistance in order to determine whether or not a neuron has been encountered. If, as determined by the resistance measurements, no neuron has been encountered 664 after the pipette distance has been repeatedly adjusted 660 and the maximum probe depth has been reached 662, the pipette is retracted 666 back to the surface for possible installation 604 of a new pipette. If, as determined by the resistance measurements, a neuron has been encountered 668, gigaseal formation stage 670 begins, starting with release 674 of positive pressure on the pipette and, if necessary, application 678 of suction pressure. Once gigaseal formation is achieved and verified 682, break-in stage 684 begins. During break-in stage 684, break-in is initiated by application 690 of a suction pulse, leading hopefully to a successful whole cell patch clamp 696. Alternatively, or in addition, a gigaseal-cell attached patch may be achieved 698.

Experimental Results.

In a preferred embodiment of the method of the invention, a pipette is placed in the holder and provided strong positive pressure, and the robot then (stage 1, "regional pipette localization") lowers the pipette at a speed of 200 μm/s to the appropriate depth for neuron hunting. It was found, as has been found previously by others, that using reasonably strong positive pressure (800-1,000 mBar) greatly improved the yield of subsequent stages. For experiments where biocytin staining was performed, using 500-600 mBar of pressure in this stage was explored, in order to reduce the amount of biocytin ejected during "regional pipette localization," and thus potentially the background staining of biocytin on non-patched neurons. This did not seem to have much effect, but such detailed modulations of pipette positive pressure over time may be worth exploring further in future algorithms.

It was found that using a high positive pressure (800-1000 mBar), greater than done in the past, greatly improved the yield of subsequent stages. Another key finding was that after the first localization stage was complete, many pipettes had slightly increased their resistances over their original values. Pipettes that acquired greater increases in resistance in this first stage had, in later stages of robot operation, more variability in their pipette resistance measurements than pipettes with smaller increases. For example, the variance between successive measurements of pipette resistance across multiple steps taken during the "neuron hunting" stage was 87±60 kΩ for pipettes that experienced zero increase in resistance acquired during the first localization stage, but was 218±137 kΩ for pipettes that experienced 500 kΩ increases, significantly more variability (mean±s.d.; $p<0.05$, t-test, n=7 trials each). By screening out pipettes that underwent large increases in pipette resistance during the first localization stage, the variability of pipette resistance measures in successive stages of robot operation can be reduced, improving the accuracy of the subsequent stages. It was found that by excluding pipettes that increased resistance by more than 300 kΩ in the first localization stage (which would result in a 136±83 kΩ measurement-to-measurement variance in the neuron hunting stage; n=123 trials), ~17% of the pipettes would be discarded (n=25 out of 148 total attempts in the main robot validation test set), but because of the low variability of later pipette resistance measurements, it became possible to detect neurons very precisely, as indicated by well-defined increases in pipette resistance, during the neuron hunting stage (stage 2).

In published neuron hunting protocols, a visually identified increase of 20-50% in pipette resistance was considered to be indicative of the presence of a viable neuron, appropriate for attempting gigaseal and break-in stages. One advantage of a robotic system is that it can analyze sequences of pipette resistance values acquired over a series of successive motor steps, thus enabling precise signatures of neuron presence that algorithmically replicate the intuitive comparisons being performed by trained human investigators. This parameter space was systematically explored, varying the number of consecutive 2 μm steps over which pipette resistance values would be considered, and also varying the numerical threshold that the pipette resistance would have to increase over these steps in order for a neuron detection to be concluded, aiming to maximize the success of manually establishing whole-cell patch clamping for each neuron-hunting procedure. Analysis of only 2 consecutive motor steps (i.e., pipette resistance data over 4 μm of travel) was found to yield noisy data, and 4 consecutive steps (i.e., over 8 μm of travel) was found to detect the neuron too late to get good recordings, perhaps because the cell was stretched. Thus, the analysis was focused on pipette resistance sequences taken over 3 consecutive steps (6 μm). Because the measurement-to-measurement variability on consecutive motor steps was about 136 kΩ, investigation thresholds of pipette resistance increase between the first and third step of 150, 200, 250, 300, 350, and 400 kΩ were selected. It was found that first-to-third step differences of at least 200-250 kΩ yielded patchable neurons at success rates of 40-45% (n=11 cells out of 25 were manually successfully gigasealed and broken-into). In contrast, 3-step sequences with <200 kΩ thresholds or >300 kΩ thresholds had much lower success rates of manual gigasealing and breaking-into (5-15% yields; 4 out of 27), perhaps due to errors in neuron detection or approach (false positives for the lower thresholds; cell stretching for the higher thresholds). Thus, or the robot a 200 kΩ threshold for pipettes of 3-5 MΩ initial resistance and 250 kΩ for pipettes of 5-9 MΩ initial resistance were chosen. In the main robot validation test set, it was found that this neuron hunting algorithm converged upon targets within the localized region 93% of the time (114 targets detected out of 123 total trials); of these 114, 56 cells ultimately resulted in a gigaseal, or a yield of 49%—similar to the 40-45% rate obtained during the pilot studies using manual validation.

For comparison purposes, the value of observing heartbeat modulation as an indication of neuronal detection was evaluated. In order to determine whether heartbeat modulation of pipette currents was also a good indicator of neuronal detection, the autopatching robot was used to record n=17 neurons, keeping attuned to the presence or absence of heartbeat modulation. All 17 neurons patched exhibited, at the point of completion of the "neuron hunting" stage, a prominent heartbeat modulation (see FIGS. 18 A-C for examples). Thus, in principle, heartbeat modulation could be added as a confirmatory check in the algorithm, although it was not found to be necessary; it appears that the algorithms' search for a monotonically increasing pipette resistance recapitulates the same essential process that takes place in the heartbeat detection procedure.

Heartbeat modulation was seen sometimes, but not always, when the patch pipette was 10 μm away from the neuron (e.g., five 2 μm steps before the pipette halted and the "neuron hunting" stage ended; FIG. 18C); this occurred 6 out of the 17 times, and may indicate that heartbeat modulation may occur even before the pipette resistance increases, and thus when a neuron has not been quite detected. This neuron-selectivity may explain why ~90% of the structures patched were neuronal, with only ~10% glial. Although most of the cells patched were neurons, the patch algorithm did not form good gigaseals typically ~50% of the time, and those targets may be with connective tissue, glia, blood vessels, etc. Notably; also analyzed were n=26 attempts in which neuron hunting halted on an object (perhaps a cell, or a piece of connective tissue), but which did not yield a gigaseal; in 24 such cases, there was no heartbeat modulation; in the remaining two cases, extreme heartbeat modulation was seen (perhaps suggesting a blood vessel to be there). In principle, future versions of the algorithm that take heartbeat modulation into account, might enable failed gigaseal trials to be ended early, thus saving several seconds per cell of time, and speeding up the robot still more.

The gigaseal formation stage (stage 3) was adapted from the best practices of prior protocols, aiming for a stereotyped sequence of steps amenable to automation. The motor was switched off after neuron hunting completion, and a 10 second wait period was imposed to see if the pipette resistance decayed back to baseline (this happened 1 time out of the 114 successful hunts; the motor simply reactivated and the neuron-hunting stage resumed). Then the positive pressure was released, suction pressure was applied if the gigaseal was not spontaneous, and the holding potential was reduced slowly to −65 mV. If a gigaseal was not apparent at the end of this procedure, the algorithm was halted (although, these could be considered loose-cell attached patches—of interest because of the excellent single cell isolation offered, even if subthreshold and synaptic events are not observable as in the whole-cell case); else, the gigaseal was left until it plateaued for at least 10-15 seconds (see FIG. 9A for example). In the main robot validation test set, of the 114 targets detected by "neuron hunting", 56 formed gigaseals (49% yield) under the operation of the robot.

The final stage is break-in (stage 4). The robot applied suction for periods of 1 second, and then precisely activated the "zap" function of the patch amplifiers (a 200 μs voltage pulse to 1 V), repeatedly every 5 seconds until the whole-cell configuration was obtained. In this scenario, the judgment of the whole cell state is reserved for a human observer, who can then halt the program. The stereotyped changes in the recording due to the cell capacitance and resistance being appended to the pipette are also quantifiable to the extent of yielding automation of program cessation, if desired. As a comparison, fully manually patched recording quality data (FIG. 16) has also been presented.

In practice, only a few zaps were needed, to establish whole cell state, so break-in could in principle be conducted in an open-loop fashion if desired. In the main robot validation test set, the 56 gigasealed neurons were split into three sets: 5 underwent spontaneous break-in without human or robot interference (thus counted as automated-whole-cell-attached trials), 24 underwent break-in using the robot, and 27 were manually broken-into in order to evaluate the success of the automated break-in procedure. Out of the 24 automatically broken-in trials, 19 successfully attained whole-cell mode (79% success); failures (5 cells) were stringently defined as a lack of break-in, "losing" the cell within 5 minutes of attaining whole-cell recording, or exhibiting >500 pA of holding current (at −65 mV). Including the trials where spontaneous break-in occurred to this dataset, automated whole-cell-attached recordings were made that met the success criteria described above 83% of the time (n=24/29). For the 27 other cells, manual whole-cell break-in was achieved in 100% of the cells using standard methods, applying brief suction pulses in rapid succession. It is clear that the objective and systematic analysis of how in vivo patch clamping occurs, coupled to precision measurement and well-timed robotic control of pipette movement and pressure control, enables automation of the steps at which humans ordinarily require extensive practice to master.

Further, a second method of automated in vivo patching using suction pulses to achieve the break-in step was developed (algorithm described in FIG. 6, data shown in FIGS. 18A-H). Once the gigaseal is established, the experimenter needs to manually increase the suction pressure in the suction port to −30 to −50 mBar; alternatively, an additional valve and an additional pressure source could be utilized. When activated, the robot applies suction for a period of 100 ms, repeatedly, every 5 seconds, until whole cell configuration is established. Out of the 30 trials where the 'suction pulse' method was employed to break-in, 25 successfully attained whole-cell mode (83.3%).

In the biocytin filling experiments, 5 neurons that were held for >15 minutes in voltage clamp mode were recorded and filled, using the criterion <<500 pA of current injection to hold at −65 mV throughout the length of the recording. A second program, after this period, retracts the pipette at a constant speed of 3 μm/s to attempt to form an outside out patch, to result in a good fill (i.e., trapping the biocytin in the cell).

Table 1 lists yields, and durations, of each of the four stages, when executed by the robot of FIG. 1, running the autopatching algorithm shown in FIG. 5, in the living mouse brain, aiming for targets in cortex and hippocampus.

TABLE 1

|  | Regional Pipette Localization | Neuron Hunting | Gigaseal Formation | Break-In |
|---|---|---|---|---|
| % age yield, whole cell patch | 81% | 93% | 51% | 82% |
| % age yield, gigaseal cell-attached | 80% | 93% | 41% | N.A |
| Duration of stage (mean ± s.d.) | 10 s | 2.2 ± 1.7 min | 2.6 ± 1.0 min | 1-10 s |

Fully automated successful attempts are defined as <500 pA of current when held at −65 mV, for at least 5 minutes; n=24 out of 73 attempts, successful gigaseal cell-attached patch clamp recording defined as a stable seal of >1 GΩ resistance; n=27 out of 75 attempts.

When validated on a final robot validation test set of neural targets within the cortex and hippocampus of anesthetized mice, the robot of FIG. 1, running the algorithm of FIGS. 5A-B, obtained successful whole-cell patch clamp recordings 32.9% of the time (defined as the holding of a cell with under 500 pA of holding current for at least 5 minutes; n=24 out of 79 attempts starting with pipette loading into the pipette holder), and successful gigaseal cell-attached patch clamp recording 36% of the time (defined as obtaining of a stable seal higher than 1 GΩ in resistance; n=27 out of 75 attempts). These success rates are similar to, or exceed, those reported by trained investigators for blind whole-cell patch clamping in vivo (for us, 28.8% success at whole-cell patching; n=17 out of 59 fully manual attempts) [see also Margrie, T. W., Brecht, M. & Sakmann, B. In vivo, low-resistance, whole-cell recordings from neurons in the anaesthetized and awake mammalian brain. *Pflugers Arch* 444, 491-498 (2002); Lee, A. K., Epsztein, J. & Brecht, M. Head-anchored whole-cell recordings in freely moving rats. *Nat. Protocols* 4, 385-392 (2009); Kitamura, K., Judkewitz, B., Kano, M., Denk, W. & Hausser, M. Targeted patch-clamp recordings and single-cell electroporation of unlabeled neurons in vivo. *Nat Meth* 5, 61-67 (2008)].

Focusing on the robot's performance after the "regional pipette localization" stage (i.e., leaving out losses due to pipette blockage during the descent to depth), the auto-patcher was successful at whole-cell patch clamping 41.8% of the time (n=23 out of 55 attempts starting with the "neuron hunting" stage), and at gigaseal cell-attached patch clamping 40.7% of the time (n=24 out of 59 attempts). From the beginning of the neuron-hunting phase, to acquisition of successful whole-cell or gigaseal cell-attached recordings, took 5±2 minutes for the robot to perform (n=47 successful recordings, similar to, or better than, the rate reported by trained investigators. The quality of the neural recordings was high, with pipette access resistances and cell leaks comparable to those of past work performed by skilled humans. Thus, the autopatcher was capable of high yields, comparable to those achieved by trained human in vivo patch clamp electrophysiologists, with speeds that can support experimental yields of many dozens of cells per day, in an automated, scalable, and parallelizable fashion.

Figure 8A:
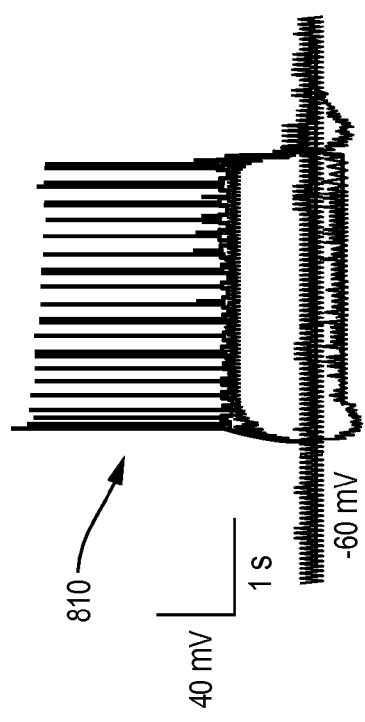
FIGS. 8A-B is an example current-clamp trace from an autopatched hippocampal neuron.
Figure 8B:
Figure 7A:
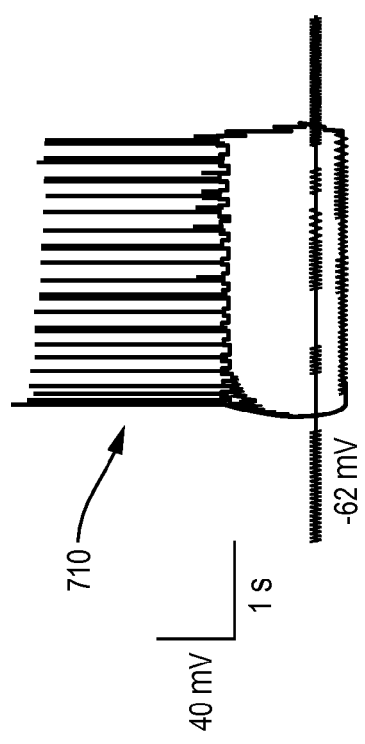
FIGS. 7A-B is an example current-clamp trace from an autopatched cortical neuron.
Figure 7B:
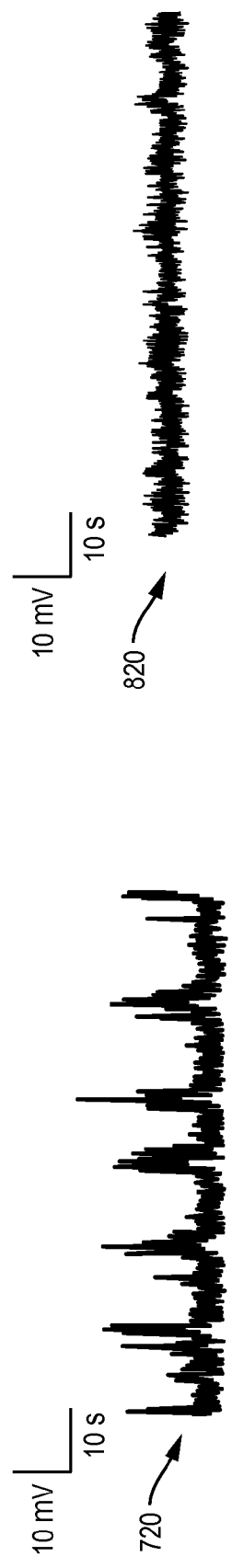

Example traces from neurons autopatched in the cortex and hippocampus are shown in FIGS. 7A-B and 8A-B, respectively. Shown in FIGS. 7A-B are current clamp traces during current injection 710 (2 s-long pulses of −60, 0, and +80 pA current injection), and at rest 720 (note compressed timescale relative to the top trace), for an autopatched cortical neuron. Access resistance is 44 MΩ; input resistance is 41 MΩ; and depth of cell is 832 μm below brain surface. Shown in FIGS. 8A-B are current clamp traces during current injection 810 (2 s-long pulses of −60, 0, and +40 pA current injection), and at rest 820, for an autopatched hippocampal neuron. Access resistance is 55 MΩ; input resistance is 51 MΩ; and depth of cell is 1,320 μm.

When biocytin was included in the pipette solution, morphologies of cells could be visualized histologically. Focusing on the robot's performance after the "regional pipette localization" stage (i.e., leaving out losses due to pipette blockage during the descent to depth), the auto-patcher was successful at whole-cell patch clamping 43.6% of the time (Table 1; n=24 out of 55 attempts starting with the "neuron hunting" stage), and at gigaseal cell-attached patch clamping 45.8% of the time (n=27 out of 59 attempts). Of the successful recordings described in the previous paragraph, approximately 10% were putative glia, as reflected by their capacitance and lack of spiking [Trachtenberg, M. C. & Pollen, D. A. Neuroglia: Biophysical Properties and Physiologic Function. *Science* 167, 1248-1252 (1970)] (4 out of 51 successful autopatched recordings; 2 out of 17 successful fully manual recordings. For simplicity, just the neurons were analyzed. From the beginning of the neuron-hunting stage, to acquisition of successful whole-cell or gigaseal cell-attached recordings, took 5±2 minutes for the robot to perform (Table 1), similar to the duration of fully manual patching (5±3 minutes; p=0.7539; n=47 autopatched neurons, 15 fully manually patched neurons).

Using the cell type criteria of Degenetais, E., Thierry, A.-M., Glowinski, J. & Gioanni, Y. Electrophysiological Properties of Pyramidal Neurons in the Rat Prefrontal Cortex: An In Vivo Intracellular Recording Study. *Cerebral Cortex* 12, 1-16 (2002) and Petilla terminology: nomenclature of features of GABAergic interneurons of the cerebral cortex. *Nat Rev Neurosci* 9, 557-568 (2008), it was found that of the 47 autopatched neuronal recordings from cortex and hippocampus analyzed in FIGS. 9A-B and FIGS. 14-16, 68% (32/47) exhibited regular spiking (RS) characteristics, 4% (2/47) exhibited burst firing patterns, 13% (6/47) exhibited irregular spike characteristics, 4% (2/47) exhibited spikes followed by smaller spikelets suggestive of back propagation of action potentials in dendritic recordings, and 2% (1/47) had accelerating spike firing characteristics. In 9% (4/47) of the neurons, steady current injection resulted a in single action potential followed by plateaued depolarizing current, with no further spike firing, indicating fast adapting neurons. It is likely that all cell recording strategies have some bias in what kinds of cells they record; extracellular recording methods, for example, might favor neurons capable of creating large extracellular fields that result in easily sortable spikes, for example.

After the "regional pipette localization" stage, pipettes that undergo increases of resistance of greater than 300 kΩ after this descent to depth are rejected, which greatly increases the yield of later steps. Then, during "neuron hunting," the key indicator of neuron presence is that as the pipette is lowered into the brain in a stepwise fashion, there is a monotonic increase in pipette resistance across several consecutive steps (e.g., a 200-250 kΩ increase in pipette resistance across three 2 μm steps). Successfully detected neurons also exhibited an increase in heartbeat modulation of the pipette current (FIGS. 17A-D), as has been noted before [Margrie, T. W., Brecht, M. & Sakmann, B. In vivo, low-resistance, whole-cell recordings from neurons in the anaesthetized and awake mammalian brain. *Pflugers Arch* 444, 491-498 (2002)], although this was not utilized in the preferred version of the algorithm due to the variability in the shape and frequency of the heartbeat from cell to cell. "Gigaseal formation" was implemented as a simple feedback loop, introducing negative pressure and hyperpolarization of the pipette as needed to form the seal. Finally, "break-in" was implemented through the application of suction and the application of a "zap" voltage pulse to enable the whole-cell state.

A plot of pipette resistance versus time for a representative autopatcher run is shown in FIG. 9A. Raw current traces resulting from the continuously applied voltage pulses, from which the pipette resistances of FIG. 9A were derived, are shown in FIG. 9B. Note the small visual appearance of the change in pipette currents (FIG. 9B) observed when a neuron is detected 910, 912. The quality of cells recorded by the autopatcher was comparable to those in published studies conducted by skilled human investigators [Margrie, T. W., Brecht, M. & Sakmann, B. In vivo, low-resistance, whole-cell recordings from neurons in the anaesthetized and awake mammalian brain. *Pflugers Arch* 444, 491-498 (2002); Lee, A. K., Epsztein, J. & Brecht, M. Head-anchored whole-cell recordings in freely moving rats. *Nat. Protocols* 4, 385-392 (2009); Harvey, C. D., Collman, F., Dombeck, D. A. & Tank, D. W. Intracellular dynamics of hippocampal place cells during virtual navigation. *Nature* 461, 941-946 (2009); DeWeese, M. R. & Zador, A. M. Non-Gaussian membrane potential dynamics imply sparse, synchronous activity in auditory cortex. *J Neurosci* 26, 12206-12218 (2006); DeWeese, M. R. Whole-cell recording in vivo. *Curr Protoc Neurosci Chapter* 6, Unit 6 22 (2007)], and to fully manually patched cells.

Shown in FIG. 9A is a representative timecourse of pipette resistance (the key parameter analyzed to control robot operation throughout the algorithm of FIG. 5) throughout a successful whole-cell patch clamp experiment performed on the autopatcher, starting with the "neuron hunting" stage 915, through gigaseal formation and break-in 920, and ending with successful whole cell attainment 925. Shown in FIG. 9A are the point when the first 910 of three resistance measurements that indicate the threshold of detection of a neuron is detected, the point when the last 912 of three resistance measurements that indicate the threshold of detection of a neuron is detected, the point 930 at which positive pressure is released during gigaseal formation, the point 935 at which suction is applied during gigaseal formation, the point at which holding potential starts to ramp down 940 from −30 mV to −65 mV, the point 945 at which holding potential hits −65 mV, and the point 950 at which break-in occurs. FIG. 9B depicts raw traces showing the currents observed going through the patch pipette, while a square voltage wave (10 Hz, 10 mV) is applied to the pipette, at the events flagged by the corresponding numerals in FIG. 9A. The resistances used throughout the algorithm for decision-making are computed by taking the average of the resistances calculated (using Ohm's law, R=(peak V)/(peak I)) from each set of five successive voltage pulses.

Figure 10:
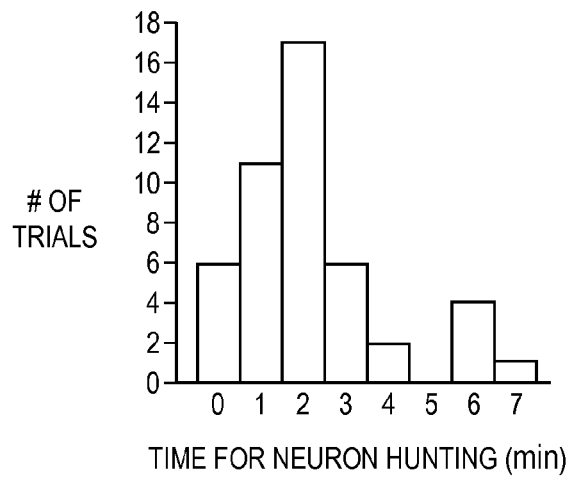
FIG. 10 is a histogram of execution times of the "neuron hunting" stage of the exemplary run of FIG. 9A.
Figure 11:
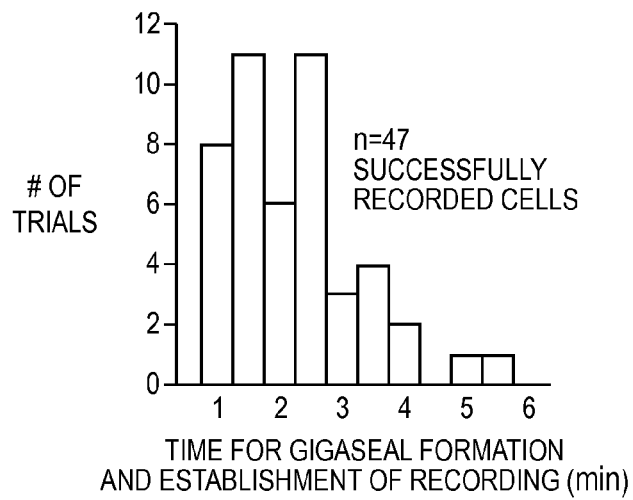
FIG. 11 is a histogram of execution times of the "gigaseal formation" and "break-in" phases of the exemplary run of FIG. 9A.
Figure 12:
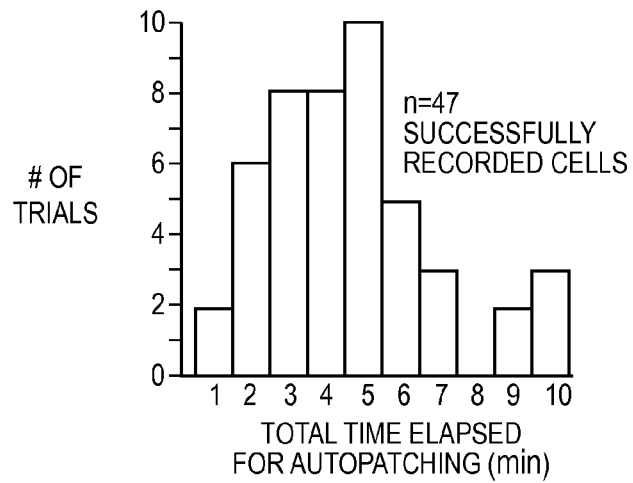
FIG. 12 is a histogram of the total execution time of the exemplary run of FIG. 9A.

FIGS. 10-12 are histograms depicting the three stages 915, 920, 925 of the exemplary experiment of FIGS. 9A-B. FIG. 10 is a histogram of execution times of the "neuron hunting" stage, showing the duration of operation of neuron hunting for the n=114 targets successfully detected during this stage. FIG. 11 is a histogram of execution times of the "gigaseal formation" and "break-in" phases, if the latter applied, for the n=47 cells for which successful cell-attached or whole-cell recordings were obtained. The "break-in" phase lasts typically just 1-10 seconds, so whole-cell recordings usually take only a little longer to obtain than do cell-attached recordings, and thus both sets of times are pooled, for simplicity, in the current histogram. FIG. 12 is a histogram of execution times for the total autopatcher algorithm starting from neuron-hunting and ending with patch attainment (i.e., the sum of the times plotted in FIGS. 10 and 11).

The entire process takes about 3.5 minutes for this cell; for the gigaseal cell-attached and whole-cell patched neurons studied in detail here, the population mean and standard deviation was 5.1±1.8 minutes from the beginning of neuron hunting to the establishment of recording (FIG. 12; n=47 neurons). The neuron-hunting stage took on average 2.5±1.7 minutes (FIG. 10, n=47), with the time to find a target that later led to successful gigaseal not differing significantly from the time to find a target that does not lead to a gigaseal (p>0.80; t-test; n=67 unsuccessful gigaseal formation trials), that is, failed trials did not take longer than successful ones. The gigaseal formation took 2.6±1.0 minutes (FIG. 11), including for the whole cell autopatched case the few seconds required for break-in; failed attempts to form gigaseals were truncated at the end of the ramp down procedure and thus took ~85 seconds. These durations are similar to those obtained by trained human investigators practicing published protocols.

FIGS. 13A-D are plots depicting the quality of autopatched in vivo neural whole cell recordings, including plots of access resistances obtained versus pipette depth and bar graph summaries of access resistances (mean±s.d.), for the final autopatcher whole cell patch validation test set, the test set in which the autopatcher concludes in the gigaseal state (data acquired after manual break-in), and the test set acquired via manual whole cell patch clamp, for cortical and hippocampal neurons. FIG. 13A depicts a plot 1310 of the access resistances (resting potential) obtained versus pipette depth and a bar graph summary 1315 of access resistances (mean±std. dev.) for the final robot validation test set of automatically whole-cell patched neurons (closed symbols; n=23), as well as for the final robot validation test set of automatically cell-attached patched neurons (open symbols, n=24, showing the data acquired after manual break-in following the conclusion of the automatic establishment of the gigaseal cell-attached state), for cortical neurons (circles; anteroposterior, 0 mm relative to bregma; mediolateral, 0-1 mm left or right of the midline; neuron hunting begins at Zu=400 μm depth) or hippocampal neurons (triangles; anteroposterior, −2 mm relative to bregma; mediolateral, 0.75-1.25 mm left or right of the midline; neuron hunting begins at Zu=1100 μm depth). FIG. 13A depicts a plot lot 1330 of the resting potentials obtained versus pipette depth and a bar graph summary 1335 of resting potentials for the neurons described for FIG. 13A. FIG. 13C depicts a plot 1350 of the holding currents obtained versus pipette depth and a bar graph summary 1355 of holding currents, for the neurons described for FIG. 13A. FIG. 13D is a logarithmic plot 1370 of the studies' holding times obtained versus pipette depth and a bar graph summary 1375 of holding times for the neurons described for FIG. 13A. Shown are both recording times that were terminated early and recording times terminated spontaneously by loss of the cell.

Figure 14:
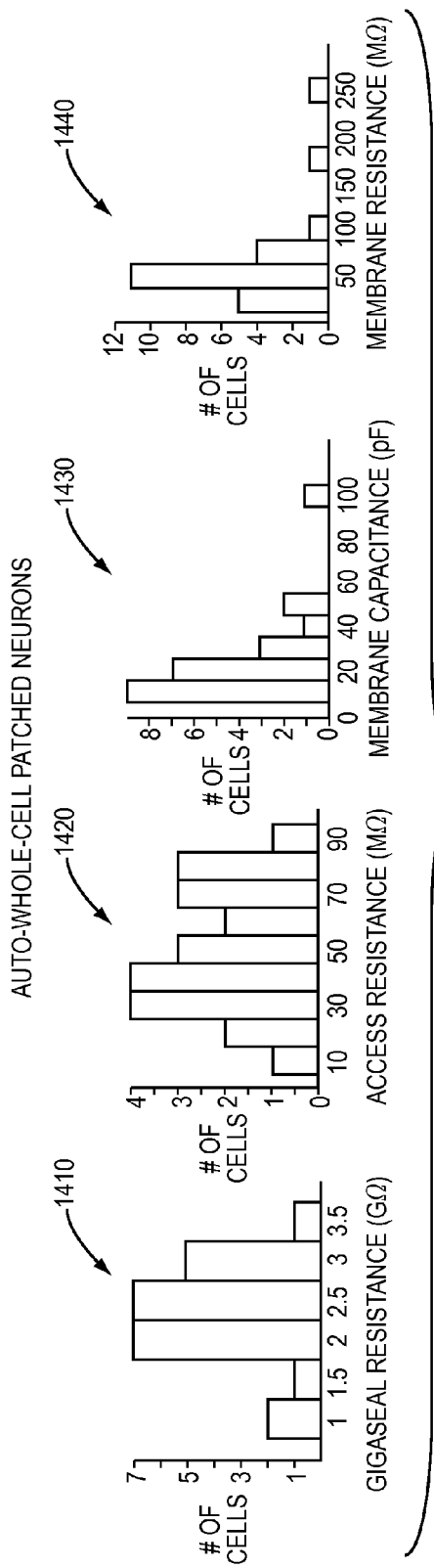
FIG. 14 depicts histograms summarizing the whole-cell patch clamp properties of the automatically whole-cell patched neurons for which recordings were automatically established in whole cell state.
Figure 15:
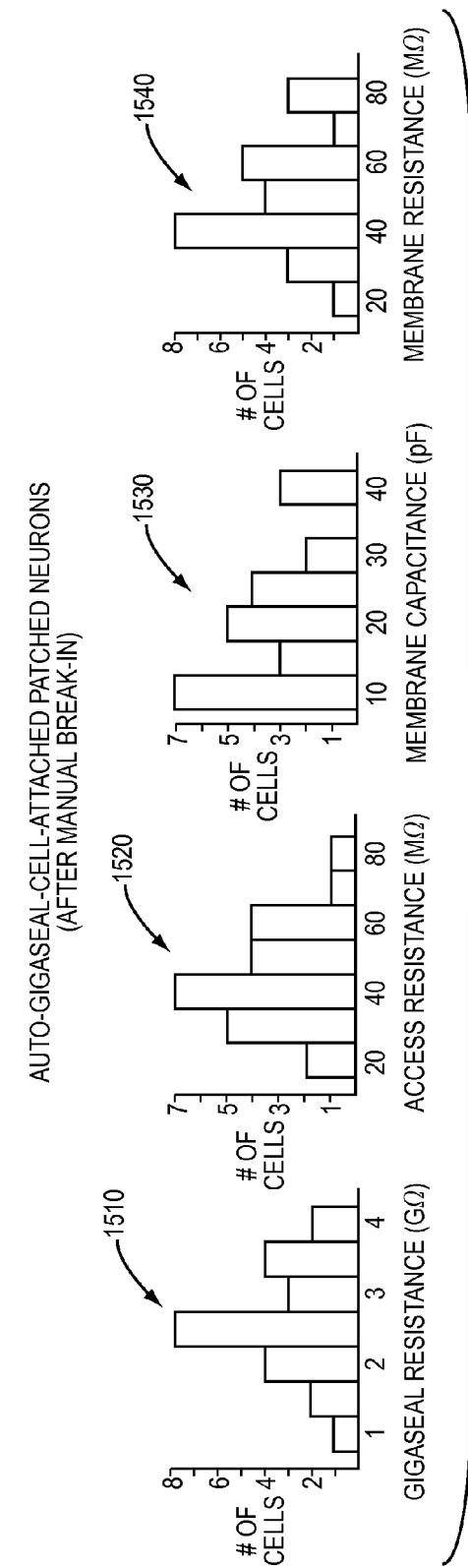
Figure 16:
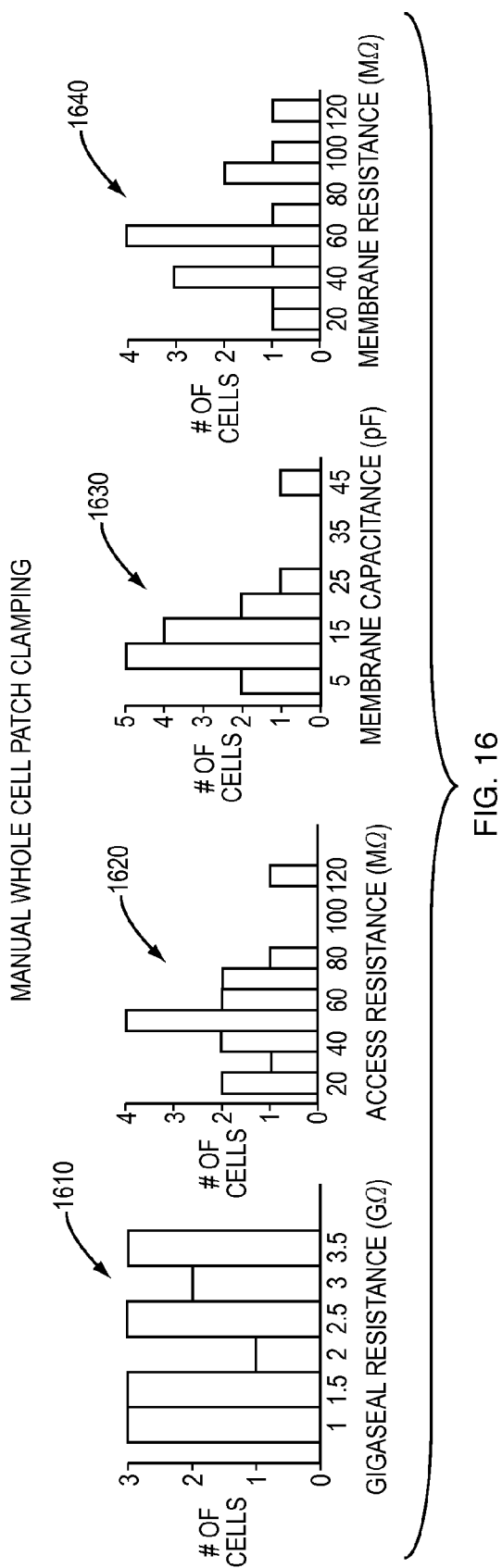
FIG. 16 is depicts histograms summarizing the whole-cell patch clamp properties of the automatically whole-cell patched neurons for which recordings were established by fully manual whole cell patch clamping.

FIGS. 14-16 are histograms summarizing the whole cell patch clamp properties of the automatically whole-cell patched neurons for which recordings were either automatically established in (FIG. 14) whole cell state (n=23 cells), (FIG. 15) gigaseal state followed by manual break-in to verify cell properties (n=24 cells), or (FIG. 16) fully manual whole cell patch clamping (n=15 cells). Properties were measured in voltage clamp at ~65 mV, including gigaseal resistance 1410, 1510, 1610 after gigaseal formation, access resistance 1420, 1520, 1620 after break-in (~5 minutes after break-in), cell membrane capacitance 1430, 1530, 1630, and cell membrane resistance 1440, 1540, 1640. The gigaseal resistances, membrane capacitances, and membrane resistances of the neurons both auto-whole-cell patched (FIG. 14) and manually broken into after auto-gigaseal-cell-attached patching (FIG. 15) spanned the ranges of what would be expected given prior cortical and hippocampal patching experiments, suggesting that with automation, the robot did not incur sacrifices in cell quality.

FIGS. 17A-D depict raw current traces recorded during "neuron hunting" stage. Shown are patch pipette currents obtained when a square voltage wave (10 Hz, 10 mV during "neuron hunting" stage) is applied to the pipette in voltage clamp mode. The left traces 1710, 1715, 1720, 1725 in FIGS. 17A-D are current traces measured 10 µm before the pipette was stopped at the end of "neuron hunting" to attempt "gigasealing". The right traces 1740, 1745, 1750, 1755 are current traces measured at the point the pipette was stopped at the end of neuron hunting. The trials depicted in FIGS. 17A-C culminated in successful whole cell patch clamp recording, while the trial depicted in FIG. 17D did not result in successful gigaseal, and subsequently was unsuccessful in establishing whole cell as well. Comparing the successful trials, while the left traces 1710, 1715 in FIGS. 17A and 17B show no heart beat modulation at distance from the neuron, the left trace 1720 in FIG. 17C shows heartbeat modulation of the current traces even 10 µm away from point of stoppage. The right traces 1740, 1745, 1750 in FIGS. 17A-C all show prominent heartbeat modulation at the point of stoppage; this is not seen in the right trace 1755 in FIG. 17D.

Once the robot has been assembled, it is easy to derive alternative or specialized algorithms (e.g., if a specialized cell type is the target, or if image-guided or other styles of patching is desired, or if the technology is desired to be combined with other technologies such as optogenetics for cell-type identification [Boyden, E. S. A history of optogenetics: the development of tools for controlling brain circuits with light. *F1000 Biology Reports* 3 (2011)]). As an example, FIG. 6 depicted a variant of the algorithm that uses pulses of suction to break in to cells, rather than "zap". The yields, cell qualities, and cell properties obtained by the suction-pulse variation of the autopatch algorithm of FIG. 6 were comparable to those obtained by the original algorithm (FIG. 5).

Figure 18E:
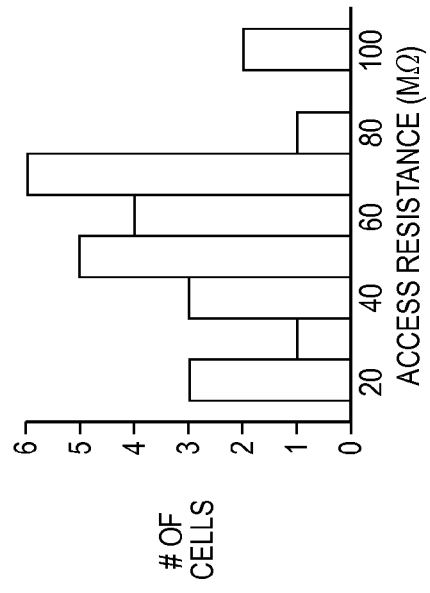
Figure 18F:
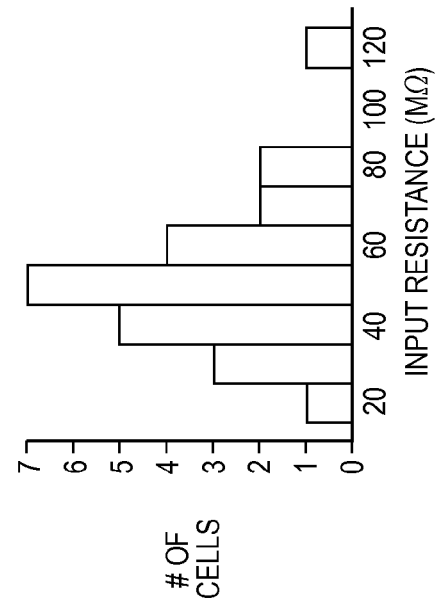
Figure 18G:
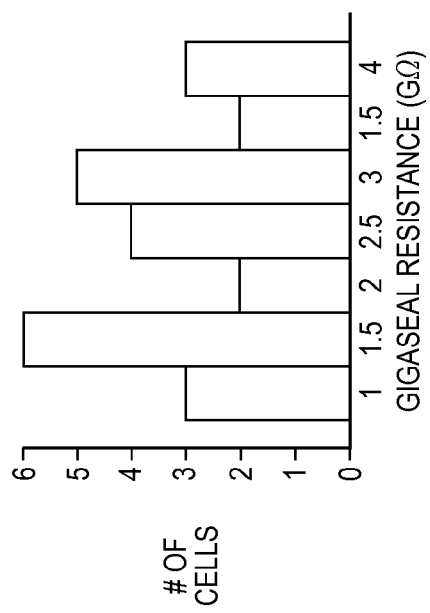
Figure 18H:
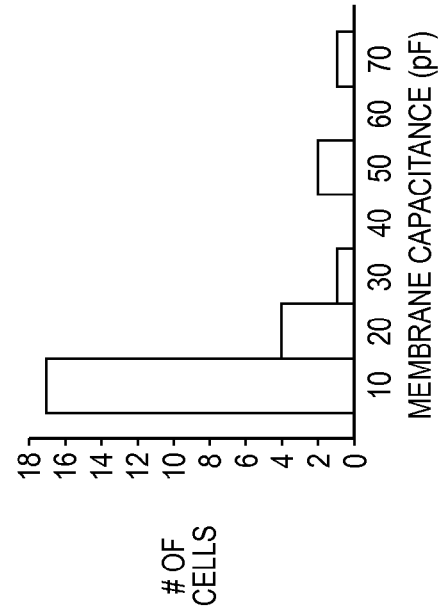

FIGS. 18A-H present results obtained using the autopatcher using the 'suction pulses' method of FIG. 6 for break-in and achieving the whole cell state. FIG. 18A is a plot of the access resistances obtained versus pipette depth for set of neurons for which whole cell state was established using the algorithm of FIG. 6, in which the "zap" is replaced by suction pulses. As seen in FIG. 18A, n=25 cortical neurons were successfully broken in to, out of 30 successful gigaseals, out of 61 total attempts starting with regional pipette localization (anteroposterior, 0 mm relative to bregma; mediolateral, 0-1 mm left or right of the midline; neuron hunting begins at 400 µm depth). Thus the break-in rate was 83% of the gigasealed neurons, and total yield from start of the algorithm was 41%. FIG. 18B is a plot of the resting potentials obtained versus pipette depth, for the neurons described in FIG. 18A. FIG. 18C is a plot of the holding currents obtained versus pipette depth for the neurons described in FIG. 18A. The recordings lasted at least 15 minutes, but the recordings were terminated early in order to focus more on the understanding of whether suction pulses would work in the autopatcher algorithm. FIG. 18D is a bar graph of average success rates obtained in each hour of recording after surgery (n=3 experimental sessions; plotted is mean+standard deviation). FIGS. 18E-H are histograms summarizing the whole cell properties of the automatically whole-cell patched neurons broken in using suction pulses method, showing good quality recordings equivalent to those obtained by zap method of break-in, measured in voltage clamp at −65 mV, including gigaseal resistance after gigaseal formation (FIG. 18E), access resistance after break-in (~5 minutes after break-in) (FIG. 18F), cell membrane capacitance (FIG. 18G), and cell input resistance (FIG. 18H).

The inherent data logging of the robot allows fine-scale analyses of the patch process, for example revealing that the probability of success of autopatching starts at 50-70% in the first hour, and then drops to 20-50% over the next few hours, presumably due to cellular displacement intrinsic to the in vivo patching process. Thus, it is anticipated that other applications of robotics to the automation of in vivo neuroscience experiments, and to other in vivo assays in bioengineering and medicine, will be possible. The ability to automatically make micropipettes in a high-throughput fashion [Pak, N., Dergance, M. J., Emerick, M. T., Gagnon, E. B. & Forest, C. R. An Instrument for Controlled, Automated Production of Micrometer Scale Fused Silica Pipettes. *Journal of Mechanical Design* 133, 061006 (2011)], and to install them automatically, might eliminate some of the few remaining steps requiring human intervention. The use of automated respiratory and temperature monitoring could enable a single human operator to control many rigs at once, increasing throughput further. As a final example, the ability to control many pipettes within a single brain, and to perform parallel recordings of neurons within a single brain region, may open up new strategies for understanding how different cell types function in the living milieu.

Statistics for evaluation of cell quality for autopatched neurons. The cell quality for both neurons automatically patched in whole cell mode, and neurons patched in gigaseal cell-attached mode, was evaluated in the main robot validation test set (n=47 successful neurons). The latter were then manually broken into in order to assess critical measures of cell and recording quality. No difference in access resistances was noted between cortex vs. hippocampus, or between auto-whole-cell patched and the auto-cell-attached-patched plus manual break-in (two-way ANOVA; main effect of region, $F_{1,45}$=0.0038, P=0.9534; main effect of break-in mode, $F_{1,45}$=1.5107, P=0.2056; interaction, $F_{1,45}$=0.7533, P=0.3583). A linear regression of pipette access resistance vs. neuron recording depth was performed, and no relationship ($R^2$=0.007, P=0.0806) was seen, suggesting that the robot performed similarly at depth as at the surface.

Statistics for comparing cell quality of autopatched neurons with fully manual patched neurons. In comparing the cell quality metrics between the n=23 auto-whole cell patched neurons and the 15 fully manually patched neurons, no difference between auto-whole-cell patched and fully manually patched neurons was noted for access resistances (two-way ANOVA; main effect of method of patching, $F_{1,33}$=0.92, P=0.5116; main effect of region (cortex vs. hippocampus), $F_{1,33}$=1.73, P=0.4175; interaction, $F_{1,33}$=0.14, P=0.706, holding current (two-way ANOVA; main effect of method of patching, $F_{1,33}$=0.83, P=0.5382; main effect of region, $F_{1,33}$=0.12, P=0.7819; interaction, $F_{1,33}$=0.38, P=0.5432), or resting membrane potential (two-way ANOVA; main effect of method of patching, $F_{1,33}$=1.16, P=0.4758; main effect of region, $F_{1,33}$=0.72, P=0.5539; interaction, $F_{1,33}$=5.873, P=0.0218). Out of the 47 neurons from which stable recordings were obtained, 14 recordings were terminated early (30-45 minutes) in order to try for more cells; for the remaining 33 cells, the recordings lasted 56.6±44.2 minutes. No difference in cell holding times was noted between auto-whole-cell patched and fully manually patched neurons (two-way ANOVA; main effect of method of patching, $F_{1,33}$=3.19, P=0.3279; main effect of region, $F_{1,33}$=0.19, P=0.7317; interaction, $F_{1,33}$=1.08, P=0.3016). Finally, no difference between auto-whole-cell patched and fully manually patched neurons was noted for gigaseal resistance (two-way ANOVA; main effect of method of patching, $F_{1,33}$=1.85, P=0.1809; main effect of region, $F_{1,33}$=0.12, P=0.7267; interaction, $F_{1,33}$=6.02, P=0.0192), cell membrane capacitance (two-way ANOVA; main effect of method of patching, $F_{1,33}$=0.96, P=0.9578; main effect of region (cortex vs. hippocampus), $F_{1,33}$=2.91, P=0.09628; interaction, $F_{1,33}$=0.7, P=0.4021), or cell input resistance (two-way ANOVA; main effect of method of patching, $F_{1,33}$=1.47, P=0.2327; main effect of region, $F_{1,33}$=0.25, P=0.2417; interaction, $F_{1,33}$=0.06, P=0.8182).

Focusing on just the data for the n=47 neurons in the main validation test set: the neuron-hunting stage took on average 2.5±1.7 minutes (n=47), with the time to find a target that later led to successful gigaseal not differing significantly from the time to find a target that does not lead to a gigaseal (P=0.8114; t-test; n=58 unsuccessful gigaseal formation trials), that is, failed trials did not take longer than successful ones. The gigaseal formation took 2.6±1.0 minutes, including for the whole cell autopatched case the few seconds required for break-in; failed attempts to form gigaseals were truncated at the end of the ramp down procedure and thus took ~85 seconds. These durations are similar to those obtained by trained human investigators practicing published protocols.

Throughput of the autopatcher. The autopatcher is not currently a "high throughput" machine in terms of sheer speed per cell, but the autopatcher can sustain its work without getting tired or bored, as a human might. A series of experiments were run, automatically recording in each of 3 mice, 7-8 successfully whole cell patch clamped neurons (total for the 3 mice, 22 successes), out of 16-20 attempts (total for the 3 mice, 52 attempts; yield, 42%); surgeries would take 41+6 minutes beginning from anesthesia of the mouse and ending with the exposed brain ready for recording; then, for each cell, pipette filling and installation (removing any used pipette, of course) would take 2±0.4 minutes, followed by the autopatcher establishing whole cell patch clamp in 5±2 minutes. The recording time for each cell was limited to 15 minutes, arbitrarily, but shorter or longer times may be of course utilized, depending on the science at hand. Thus, the amount of time required to record n neurons successfully, for a desired recording time T, would be approximately $$40+n/0.42*7+n/0.42*T$$

minutes. (The surgeries, of course, could be done in advance to equip mice with headplates to minimize day-of-recording time expenditure.) Thus, during an 8 hour day, ~25 neurons might be successfully recordable in a single mouse, if the recording times were very short; this doesn't take into account the important consideration of cell displacement that could result from an electrophysiological experiment, thus reducing yield over time.

Strategies can be devised to limit the impact of cell displacement or damage from impacting yield; for example, patching neurons in higher regions before patching those in lower ones. The autopatcher travels, on average, 150±112 microns in the cortex during the neuron hunt phase, before hitting the neuron (n=22 cells); this short travel distance suggests that the pipette might well be hitting the very first cell that it is allowed to encounter (e.g., is approaching under low pressure). Smaller diameter pipettes, even down to 100-200 microns in diameter, are easily available (albeit more difficult for humans to handle), and so this might not be a fundamental limit on scale. It is possible that patching neurons in varying brain regions could result in very high fidelity recordings. Finally, if, for example, it takes 2 minutes to load a pipette, and 5 to obtain a cell and another T minutes to do a recording, it would in principle be possible for a single individual to run (5+T)/2 rigs at once; for 15 minute recording times, that would make for 10 rigs being simultaneously controlled by one employee.

Detailed description of implementation and operational details of the prototype used to produce the reported experimental results.

The prototype apparatus used to produce the reported experimental results is depicted in FIG. 3. While specific parts, software, and implementation details for this prototype are described herein, it will be clear to one of skill in the art of the invention that many other comparable parts, software, and implementation methodologies exist and would be equally suitable for use in the present invention. Specific parts used for this prototype include:

1. Patch clamp amplifier: Multiclamp 700B (Molecular Devices)
2. Patch clamp headstage: CV-7B (Molecular Devices)
3. Primary computer interface board: Digidata 1440B (Molecular Devices)
4. Secondary computer interface board: NI USB-6259-BNC (National Instruments)
5. 3 axes linear actuator for manual positioning: MX7600L (Siskiyou)
6. Programmable linear actuator with controller kit: PZC200-KT (Newport)
7. Linear stage: MX460A-X (Newport)
8. Electronic 2-way solenoid valves: LDA0533215H-A (Lee company)
9. BNC relay switch: CX230 (Tohtsu)

Installing programmable motor in standard in vivo electrophysiology setup. To install a programmable linear motor in the in vivo electrophysiology rig, a custom dovetail groove mounting plate was machined to fix the CV 7B headstage to the Newport linear stage that is controlled using the piezo-motor. The entire assembly was then mounted onto the 3 axes linear actuator (Siskiyou Inc), as shown in FIGS. 1 and 3. The motor was connected to the controller and interfacing with the computer was done as per the instructions in the NanoPZ system user manual provided by Newport Corporation.

Figure 19:
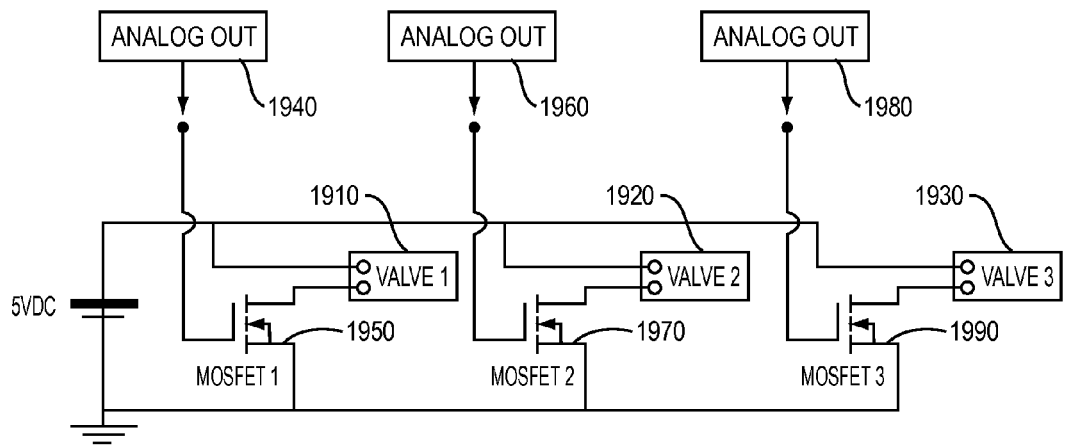
FIG. 19 is a circuit diagram for actuation of the solenoid valves in the prototype embodiment of FIG. 3.

The circuit diagram for actuation of the solenoid valves is shown in FIG. 19. The pneumatic connections are shown in FIG. 2. The steps used to make the connections, as shown in FIG. 19, are:
1) Connect the Common port (output) of Valve 1 1910 to pipette holder.
2) Connect the Common port (output) of Valve 2 1920 to normally open (N.O.) input port of Valve 1 1910.
3) Connect the Common port (output) of Valve 3 1930 to normally closed (N.C.) input port of Valve 1 1910.

The steps used to implement computer control of the bank of valves were:
1) Connect Analog Out 1 (AO1) 1940 of the USB 6259-BNC to Gate of MOSFET 1 1950 to drive Valve 1 1910.
2) Connect Analog Out 2 (AO2) 1960 of the USB 6259-BNC to Gate of MOSFET 2 1970 to drive Valve 2 1920.
3) Connect Analog Out 3 (AO3) 1980 of the USB 6259-BNC to Gate of MOSFET 3 1990 to drive Valve 3 1930.

Interfacing Amplifier to computer. The signals for the Multiclamp 700B amplifier (Molecular Devices) are sent to and from two computer interface boards. The NIDAQ USB-6259-BNC (National instruments) board is used to send signals to the amplifier during Autopatcher operation, and the Digidata 1440A is used for recording with commercial software Pclamp (Molecular Devices) once whole cell is obtained. For this dual interface:
1) Connect Analog Out 0 (AO0) of the NIDAQ USB-6259 to the channel A of the BNC relay switch.
2) Connect the Analog out 0 (AO0) of the Digidata 1440B to channel B of the BNC relay switch.
3) Connect the output of the BNC relay switch to the command input of the Multiclamp 700B amplifier.
4) Connect Digital Out Ch0 of the NIDAQ board to the BNC relay input.
5) Connect the primary scaled output of Multiclamp 700B to Analog IN 1 (AI 1) of the NIDAQ USB-6259 and analog input 0 (AI1) of the Digidata 1440B.

In the default configuration, the input command to the patch amplifier is sent from the NIDAQ board for automated patch clamping. Once a whole cell configuration is established, the toggle in "Command_switch.vi" program can be used to switch the inputs and data can be recorded in current clamp or voltage clamp using the clampex software.

Initial Program Setup. The Autopatcher program was developed in the Labview 8.6 (National Instruments) programming environment, running on a Windows XP or later operating system. The Autopatcher prototype implementation in its current form thus requires a version 8.6 or higher version of Labview to run. Install the NiDAQmx driver for the USB-6259 data acquisition board. For serial communication with the motor controller, labview VISA must be installed.

The following instructions are an exemplary methodology to be followed for setting up the program for automated whole cell patch clamping in vivo and represent the method employed using the prototype of FIG. 3 to obtain the presented experimental results.

Figure 20:
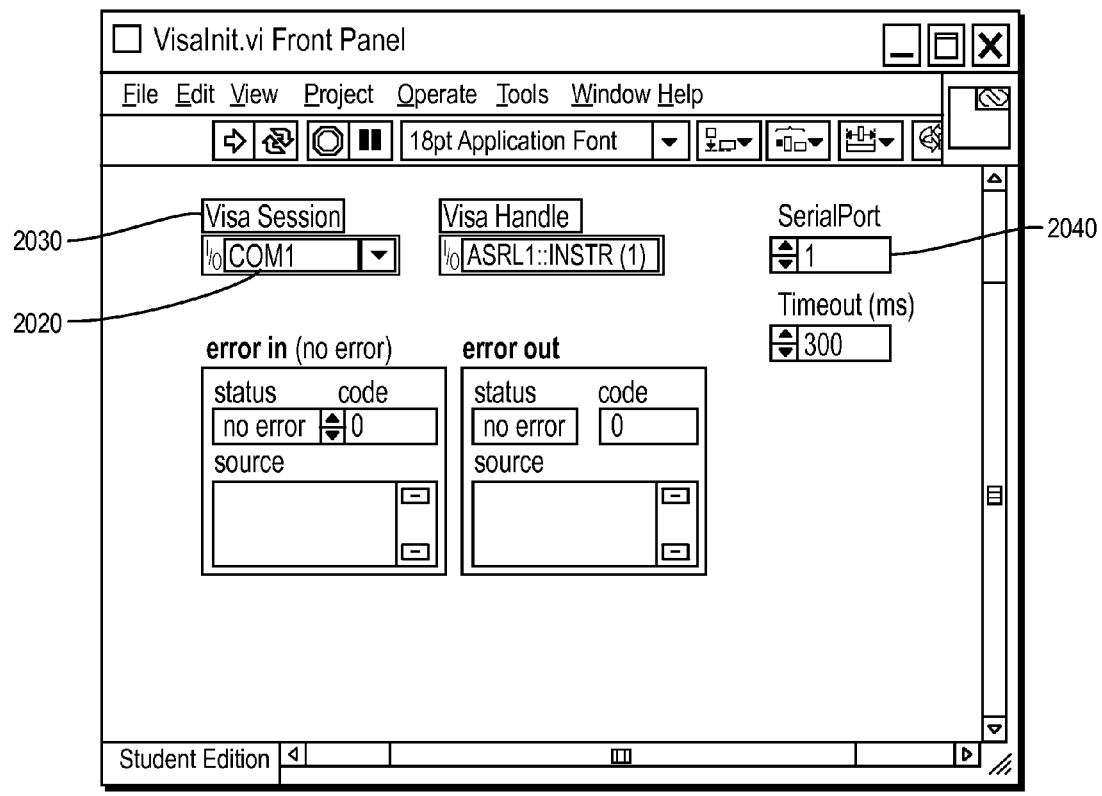
FIG. 20 is a screen shot of the user interface for the program that initiates serial communication with motor controller in the prototype embodiment of FIG. 3.

Establishing serial communication with motor controller.
1) Open Autopatcher_library.llb in labview library manager window. This contains all files that are called by the main program during autopatching. All files that need to be opened during the course of operation of the Autopatcher can be accessed using this project manager.
2) Open "VisaInit.vi". FIG. 20 is a screen shot of the "Visainit.vi" program that is used to initiate serial communication with motor controller.
3) Specify the COM port number 2020 in the Visa Session 2030 and corresponding serial port number 2040 to which the motor controller is connected to in the computer, and run the program.

User Settings in the "Autopatcher_ver1.0.vi". From the same library, open "Autopatcher_ver1.0.vi". The user interface for the Autopatcher program has 4 tabs: (a) Control panel, (b) Neuron hunt, (c) Seal formation and (d) Break-in.

Figure 21:
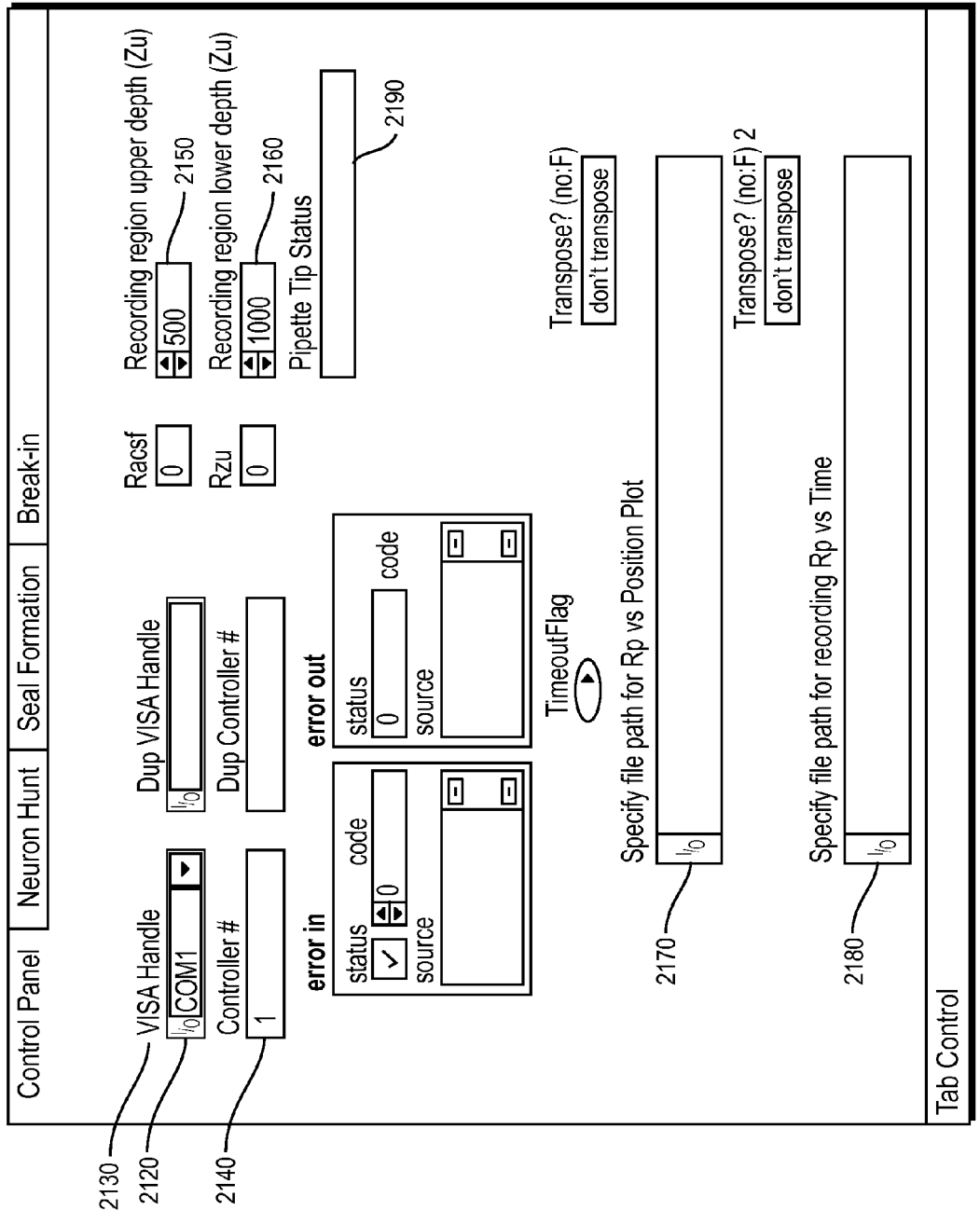
FIG. 21 is a screen shot of the control panel tab of the Autopatcher program in the prototype embodiment of FIG. 3.

Control Panel Tab Settings. FIG. 21 is a screenshot of the control panel tab of the Autopatcher program. This is a debug-oriented version of the Autopatcher software, allowing parameters to be changed; if parameters are not going to be changed, it will be clear to one of skill in the art that these parameters could be hardwired into the code.
 1. Specify the COM port 2120 that was initialized in the "VisaInit.vi" program in the Visa Handle 2130 scroll down menu option.
 2. Enter Controller number 2140 as 1.
 3. Specify the upper depth 2150 (Zu in micrometers) of the region you want to record from.
 4. Specify the lower depth 2160 (Zl in micrometers) of the region you want to record from. During operation, the Autopatcher will lower the pipette to Zu and start scanning for neurons. It will stop at Zl if no neuron is encountered in that range.
 5. There are two file path dialog boxes 2170, 2180 to specify the location in which the plot of Pipette resistance as a function of depth 2170 (during neuron hunting) and pipette resistance as a function of time 2180 (during attempted gigaseal formation) are stored. Specify these file paths 2170, 2180 as needed. Pipette Tip Status 2190 will be displayed during program operation.

Figure 22:
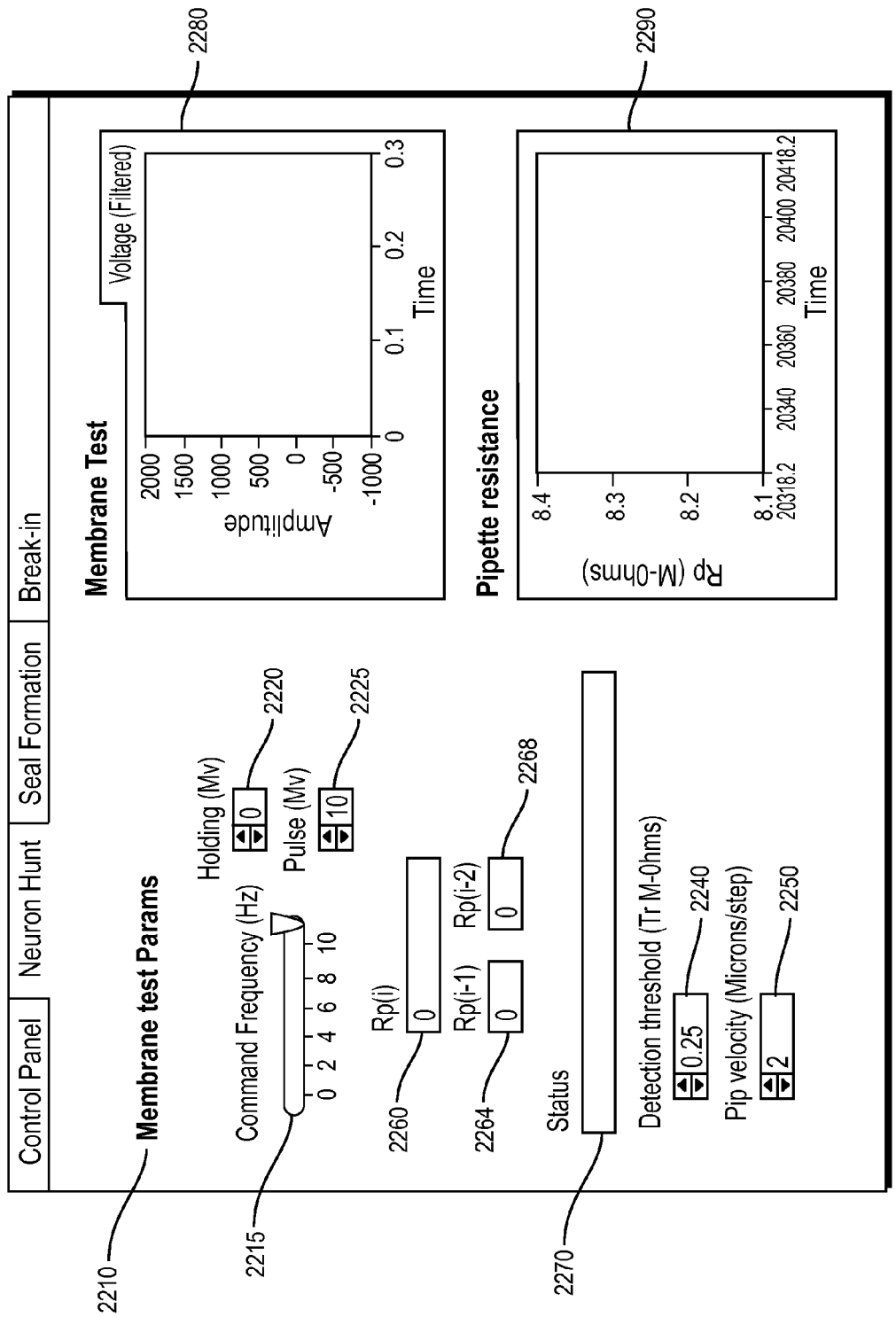
FIG. 22 is a screen shot of the Neuron Hunt tab in the Autopatcher program in the prototype embodiment of FIG. 3.

Neuron Hunt Tab Settings. FIG. 22 is a screenshot of the Neuron Hunt tab in the Autopatcher program.
 1. Specify the membrane test parameters 2210 in a manner similar to the Membrane test done in Pclamp. (e.g., Command frequency 2215=10 Hz, Holding 2220=0 mV, Pulse 2225=10 mV)
 2. Set detection threshold 2240 between 0.2-0.3, as required.
 3. Set pipette velocity 2250 at 2 micrometers/step.
This tab displays the last three pipette resistance readings: Rp (i) 2260, Rp (i−1) 2264, and Rp (i−2) 2268. Status bar 2270 indicates the current state of the program execution (i.e., 'Hunting for neurons at desired depth' or 'Neuron found'). Two graphical charts 2280, 2290 are provided that plot the currents flowing through the pipette (Membrane test 2280) and the pipette resistance 2290 as a function of position in the brain.

Figure 23:
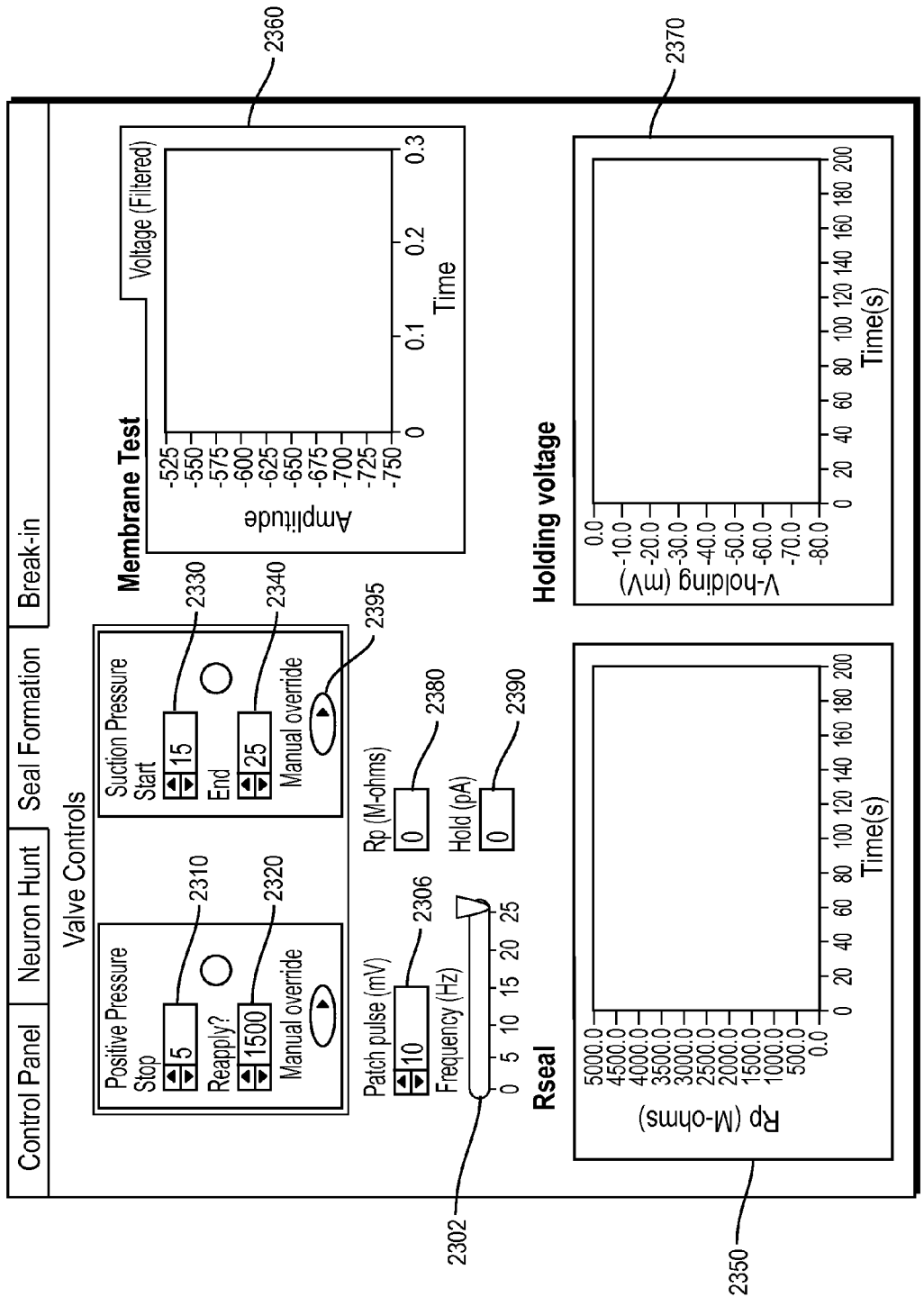
FIG. 23 is a screen shot of the Break-in tab in the Autopatcher program in the prototype embodiment of FIG. 3.

Seal Formation Tab Settings. FIG. 23 is a screenshot of the Seal formation tab in the Autopatcher program.
 1. Specify the membrane test parameters in a manner similar to the Membrane test done in Pclamp (e.g., Command frequency 2302=10 Hz, Holding=0 mV, Pulse 2306=10 mV).
 2. Set the time 2310 at which positive pressure is released. In all of the experiments reported herein, it was set at 10 seconds. Similarly, set the time 2320 at which positive pressure needs to be reapplied if needed. In all experiments, it was set at an arbitrarily large value (~1500 seconds).

3. Set the times at which suction pressures need to be applied 2330 and removed 2340 (15 s and 25 s respectively in the example shown).

In this tab, there are three graphical charts 2350, 2360, 2370 that plot the pipette resistance 2350, the current flowing though the pipette during membrane test 2360, and the holding potential 2370. Two numerical indicators 2380, 2390 display the most recent pipette resistance (Rp) 2380 and holding current 2390 values.

Figure 24:
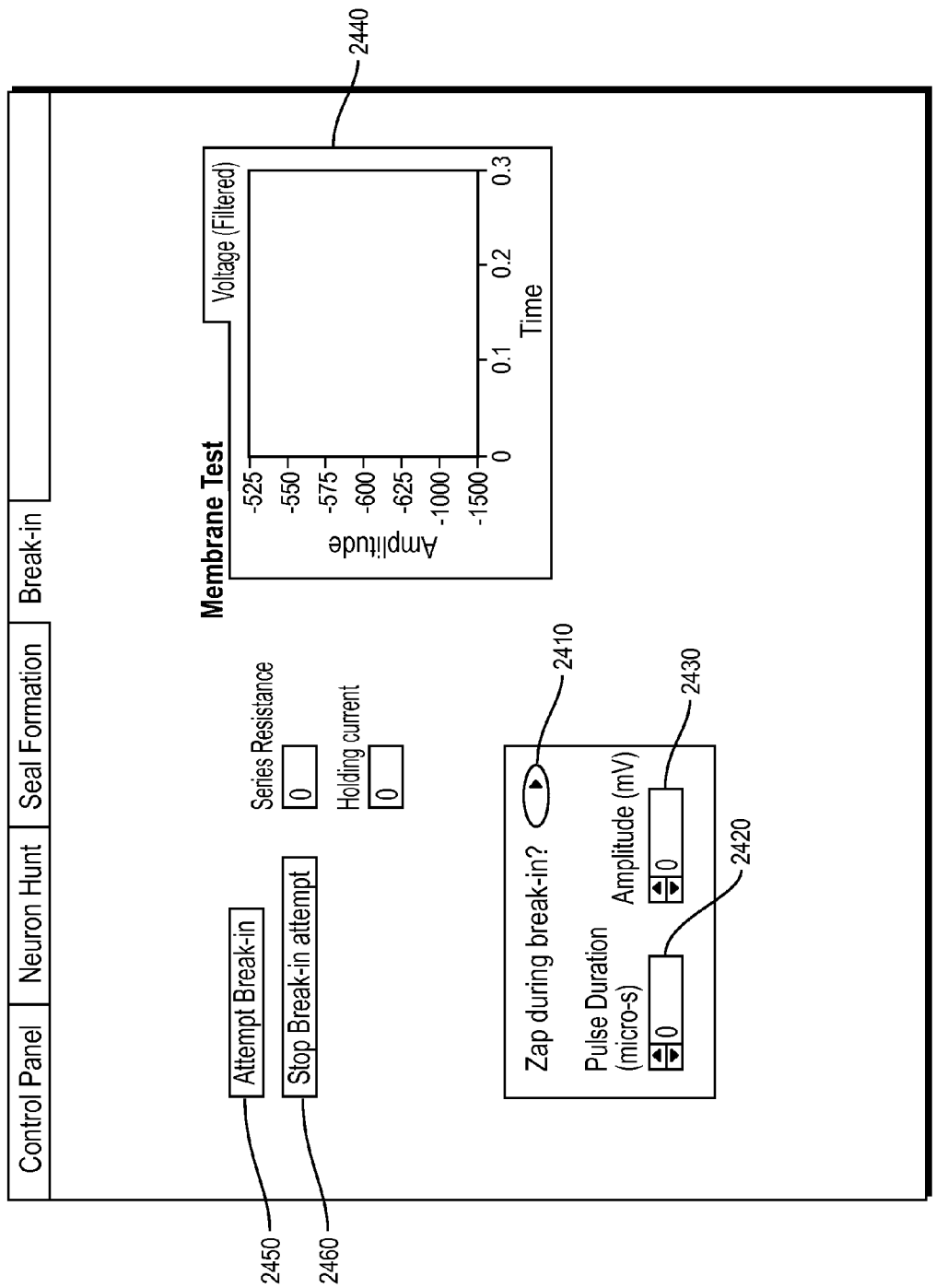
FIG. 24 is a screen shot of the Break-in tab in the Autopatcher program in the prototype embodiment of FIG. 3.

Break-in Tab Settings. FIG. 24 is a screenshot of the Break-in tab in the Autopatcher program.
1. Specify whether it is desired to zap 2410 during break-in, or break-in using suction pulses only.
2. If zap function 2410 is used, specify the pulse duration 2420 (e.g., 200 ms) and amplitude 2430 (e.g., 1000 mV).

A graphical chart that displays the membrane current 2440 is provided to determine whether break-in has occurred or not. Once these settings were input for the first trial, they remained the same for the rest of the trials.

Manual Tasks before running the Autopatcher program.
1. Fill patch pipette with internal saline solution and install in pipette holder.
2. Open and run "valve_reset.vi" to reset all valves to default configuration.
3. Application of pressures:
   i. Apply High positive pressure at N.O. port of Valve 2.
   ii. Apply Low positive pressure at N.C. port of Valve 2.
   iii. Apply suction pressure at N.C. port of valve 3.

It should be ensured that the pipette does not have any debris (particularly AgCl flakes) inside the pipette. Internally clogged pipettes typically have varying resistance readings that may interfere with proper functioning of the Autopatcher. In the default configuration, the valve system outputs high positive to the pipette to ensure that the tip does not get blocked accidentally.

4. Position pipette in the center of the craniotomy, 20-30 micrometers above the brain surface using a stereomicroscope for visualization. Ensure the pipette tip does not touch the brain surface as this will result in erroneous baseline resistance measurement.
5. Open the Multiclamp 700B commander program (FIG. 24).
6. Make sure the amplifier is in Voltage clamp mode by selecting VC mode button.
7. Ensure Holding current is set at 0 mV.
8. Reset the pipette offset by using the Auto pipette offset function.
9. Neutralize for pipette capacitance by Auto correcting for Cp Fast and Cp.
10. Run membrane test.vi in continuous run mode and monitor the resistance of the pipette for 30-60 second. The resistance value should be between 3-9 M$\Omega$, and read a constant value throughout this period. If the pipette is internally clogged with AgCl flakes or other debris, the resistance value typically keeps increasing gradually, or might vary significantly (>500 K$\Omega$) enough to interfere with proper functioning of the Autopatcher program. In that case, replace the pipette. Ensure pipettes are not getting internally clogged before repeated attempts at autopatching.

The Autopatcher program can now be run for Automated whole cell patch clamping in vivo.

Figure 25:
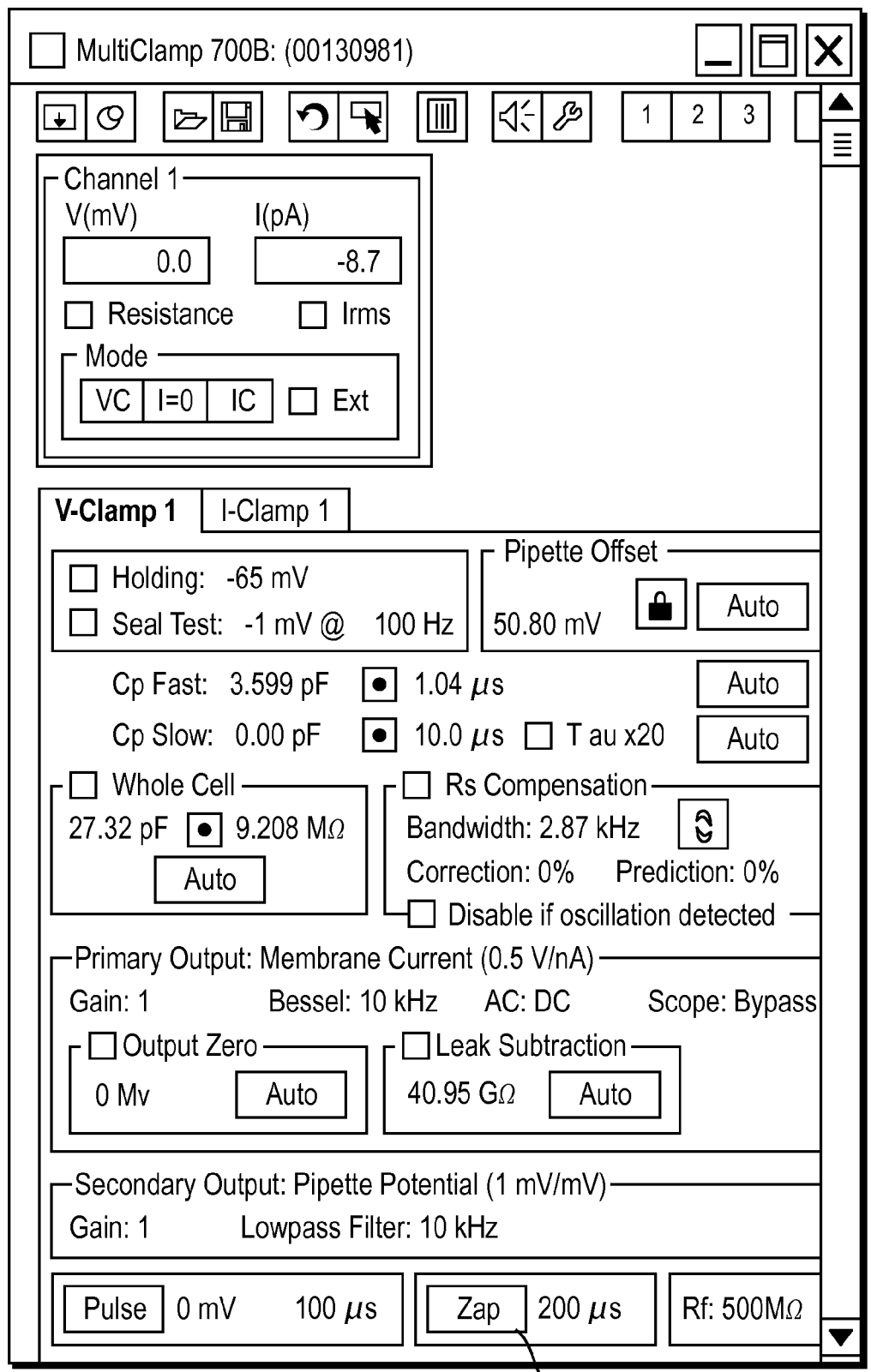
FIG. 25 is a screen shot of the settings in the Multiclamp commander before the Autopatcher program is executed in the prototype embodiment of FIG. 3.

FIG. 25 is a screenshot of settings in the Multiclamp commander before Autopatcher program is executed. Open and run "Command_switch.vi". Run this continuously during entire experiment. At any time, the command input going to the Multiclamp 700B can be switched between NIDAQ USB 6259 (for autopatching) and Digidata 1440B (for post patch recording) using software controls.

Running the Autopatcher Program. Select the control panel tab (FIG. 21) and run the Autopatcher_ver1.0 program in Labview, making sure all the setting in the tabs are specified.

1) The Autopatcher measures and displays the pipette resistance Racsf outside the brain.
2) The pipette is then lowered to the specified depth Zu under high positive pressure.
3) The pressure is lowered to low positive pressure and the pipette resistance Rzu is measured to check for blockage.
4) If the pipette is blocked, "Pipette blocked, install new pipette" message is displayed under Pipette Tip Status 2190. It is then retracted back and the program stops. Install a new pipette, and performs the manual tasks described previously before restarting the Autopatcher.
5) If the pipette is not blocked, "Pipette not blocked" message is displayed under Pipette Tip Status 2190, and the Autopatcher initiates Neuron Hunt. Switch to the 'Neuron Hunt' tab (FIG. 22).
6) The Autopatcher now moves the pipette in steps specified by the user (e.g., 2 micrometers) and measures the pipette resistance at each step. Autopatcher either stops pipette actuation when a neuron is encountered or when it has scanned through to depth Zl without encountering a neuron. In the latter case the program stops. If a neuron is encountered, the Autopatcher initiates Seal formation protocol. Switch to 'Seal formation' tab (FIG. 23).
7) The pipette resistance can be monitored over time in the Rseal graph 2350 indicator. Release of positive pressure and application of suction, as well as ramp down of holding potential takes place. Typically in a successful attempt, a gigaseal is formed and holding voltage 2390 is ramped down to −65 mV in 80 seconds. At the end of 80 seconds, if seal resistance 2380 is less than a gigaohm, stop program. Retract pipette using the manual xyz positioner. A new trial can be started by installing a new pipette.
8) If a break-in occurs spontaneously, stop the program and go to Step 11.
9) If break-in does not occur spontaneously, switch to the Break-in tab (FIG. 24). If attempting to break-in using suction pulses, restore the suction pressure in the suction port. Then press 'Attempt break-in' 2450. The Autopatcher will apply suction pressure for 100 ms. If successful, typical membrane current transients can be seen in the graph indicator 2440. A similar procedure is followed for break-in using the zap function. If unsuccessful, press stop break-in attempt 2460 after 5 seconds, and retry 2450 until successful break-in occurs. Alternately, break-in can be achieved by using the manual override 2395 of suction pressure option in the Gigaseal formation tab (FIG. 23) and applying the requisite voltage zap using the 'Zap' button 2520 in the Multiclamp commander (FIG. 25). If using this option, make sure the manual override 2395 is switched off after break-in, else the cell contents may be dialized into the pipette.
10) Once a whole cell recording is established, stop program.
11) Set the amplifier to I=0 mode using the Multiclamp commander (FIG. 25) software and select clampex in the front panel of the "Command_switch.vi" program that was initiated in Step 4. This will automatically enable the command input to the amplifier to be sent by the Digidata 1440B. Whole cell recordings in voltage clamp or current clamp can be carried out in using Pclamp software (Molecular Devices).

Biocytin Filling Experiments. After a neuron has been recorded in whole cell mode for a sufficiently long period of time to fill it with biocytin (~10 minutes), the "Retract_pipette.vi" program can be run to attempt to form an outside out patch. The program has two user set distances.

1) Specify the distance you want to retract the pipette at a slow speed (e.g., 3 µm/s).
   Typically, it was set at 100-150 µm to get an outside out patch.
2) Specify the distance the pipette is to be rapidly retracted, typically set to the depth of the recording, as noted while running the "Autopatcher_ver1.0.vi".
3) Run the program. The program will first retract the pipette at steps of 3 µm every second for the distance specified by the user. Once that distance is reached, the program rapidly retracts the pipette by the distance specified in Step 2.

Detailed description of the methodology used to obtain the reported experimental results.

Surgical procedures. Adult male C57BL/6 mice (Taconic), 8-12 weeks old, were anesthetized using ketamine/xylazine (initially at 100 mg/kg and 10 mg/kg, and redosed at 30-45 minute intervals with 10-15% of the initial ketamine dose as needed, using toe pinch reflex as a standard metric of anesthesia depth). The scalp was shaved, and the mouse placed in a custom stereotax, with ophthalmic ointment applied to the eyes, and with Betadine and 70% ethanol used to sterilize the surgical area. Three self-tapping screws (F000CE094, Morris Precision Screws and Parts) were attached to the skull and a plastic headplate affixed using dental acrylic, as previously described [Boyden, E. S. & Raymond, J. L. Active reversal of motor memories reveals rules governing memory encoding. *Neuron* 39, 1031-1042 (2003)]. Once set (~20 minutes), the mice were removed from the stereotax and placed in a custom-built low profile holder. A dental drill was used to open up one or more craniotomies (1-2 mm diameter) by thinning the skull until ~100 µm thick, and then a small aperture was opened up with a 30 gauge needle tip. Cortical craniotomies occurred at stereotaxic coordinates: anteroposterior, 0 mm relative to bregma; mediolateral, 0-1 mm left or right of the midline; neuron hunting began at 400 µm depth. Hippocampal craniotomies occurred at stereotaxic coordinates: anteroposterior, −2 mm relative to bregma; mediolateral, 0.75-1.25 mm left or right of the midline; neuron hunting began at 1100 µm depth. It is critical to ensure that bleeding is minimal and the craniotomy is clean, as this allows good visualization of the pipette, and minimizes the number of pipettes blocked after insertion into the brain. The dura was removed using a pair of fine forceps. The craniotomy was superfused with artificial cerebrospinal fluid (ACSF, consisting of 126 mM NaCl, 3 mM KCl, 1.25 mM $NaH_2PO_4$, 2 mM $CaCl_2$, 2 mM $MgSO_4$, 24 mM $NaHCO_3$, and 10 mM glucose), to keep the brain moist until the moment of pipette insertion.

Seventeen mice were used to derive the autopatching algorithm (FIG. 5). Sixteen mice were used to validate the robot for the primary test-set. For the manual experiments, 4 mice were used. For the development of the suction-based autopatching variant (FIG. 6), 5 mice were used. Out of the 5 mice used for suction-based autopatching, 3 mice were used for the throughput estimations. For biocytin filling experiments and validation of heartbeat modulation as a method for confirming neuronal detection, 6 additional mice were used.

At the end of the patch clamp recording, mice were euthanized, while still fully anesthetized, via cervical dislocation, unless biocytin filling was attempted. In the case of biocytin filling, the mice were isoflurane anesthetized, then transcardially perfused in 4% ice-cold through the left cardiac ventricle with ~40 mL of ice-cold 4% paraformaldehyde in phosphate buffered saline (PBS).

Electrophysiology. Borosilicate glass pipettes (Warner) were pulled using a filament micropipette puller (Flaming-Brown P97 model, Sutter Instruments), within a few hours before beginning the experiment, and stored in a closed petri dish to reduce dust contamination. Glass pipettes with resistances between 3-9 MΩ were pulled. The intracellular pipette solution consisted of (in mM): 125 potassium gluconate (with more added empirically at the end, to bring osmolarity up to ~290 mOsm), 0.1 $CaCl_2$, 0.6 $MgCl_2$, 1 EGTA, 10 HEPES, 4 Mg ATP, 0.4 Na GTP, 8 NaCl (pH 7.23, osmolarity 289 mOsm), similar to what has been used in the past. For experiments with biocytin, 0.5% biocytin (weight/volume) was added to the solution before the final gluconate-based osmolarity adjustment, and osmolarity then adjusted (to 292 mOsm) with potassium gluconate. Manual patch clamping was performed using previously described protocols [DeWeese, M. R. Whole-cell recording in vivo. *Curr Protoc Neurosci* Chapter 6, Unit 6 22 (2007); Margrie, T. W., Brecht, M. & Sakmann, B. In vivo, low-resistance, whole-cell recordings from neurons in the anaesthetized and awake mammalian brain. *Pflugers Arch* 444, 491-498 (2002)], with some modifications and iterations in order to prototype algorithm steps and to test them.

Robot construction. The autopatcher was assembled through modification of a standard in vivo patch clamping system. The standard system comprised a 3-axis linear actuator (MC1000e, Siskiyou Inc) for holding the patch headstage, and a patch amplifier (Multiclamp 700B, Molecular Devices) that connects its patch headstage to a computer through a analog/digital interface board (Digidata 1440A, Molecular Devices). For programmable actuation of the pipette in the vertical direction, a programmable linear motor (PZC12, Newport) was mounted onto the 3-axis linear actuator. For experiments where biocytin filling was attempted, the programmable linear motor was mounted at a 45° angle to the vertical axis, to reduce the amount of background staining in the coronal plane that histological sectioning was done along. The headstage was in turn mounted on the programmable linear motor through a custom mounting plate. The programmable linear motor was controlled using a motor controller (PZC200, Newport Inc) that was connected to the computer through a serial COM port.

An additional data acquisition (DAQ) board (USB 6259 BNC, National Instruments Inc) was connected to the computer via a USB port, and to the patch amplifier through BNC cables, for control of patch pipette voltage commands, and acquisition of pipette current data, during the execution of the autopatcher algorithm. During autopatcher operation, the USB 6259 board sent commands to the patch amplifier; after acquisition of cell-attached or whole-cell-patched neurons, the patch amplifier would instead receive commands from the Digidata. A software-controlled TTL co-axial BNC relay (CX230, Tohtsu) was used for driving signal switching between the USB 6259 BNC and the Digidata, so that only one would be empowered to command the patch amplifier at any time. The patch amplifier streamed its data to the analog input ports of both the USB DAQ and the Digidata throughout and after autopatching. For pneumatic control of pipette pressure, a set of three solenoid valves (2-input, 1-output, LHDA0533215H-A, Lee Company) was used. They were arranged, and operated, in the configuration shown in FIG. 2. The autopatcher program was coded in, and run by, Labview 8.6 (National Instruments). The USB6259 DAQ sampled the patch amplifier at 30 KHz and with unity gain applied, and then filtered the signal using a moving average smoothening filter (half width, 6 samples, with triangular envelope), and the amplitude of the current pulses was measured using the peak-to-peak measurement function of Labview. During the entire procedure, a square wave of voltage was applied, 10 mV in amplitude, at 10 Hz, to the pipette via the USB6259 DAQ analog output. Resistance values were then computed, by dividing applied voltage by the peak-to-peak current observed, for 5 consecutive voltage pulses, and then these 5 values were averaged. Once the autopatch process was complete, neurons were recorded using Clampex software (Molecular Devices). Signals were acquired at standard rates (e.g., 30-50 KHz), and low-pass filtered (Bessel filter, 10 KHz cutoff). All data was analyzed using Clampfit software (Molecular Devices) and MATLAB (Mathworks).

Robot Operation. At the beginning of the experiment, a pipette was installed and filled with pipette solution using a thin polyimide/fused silica needle (Microfil) attached to a syringe filter (0.2 μm) attached to a syringe (1 mL). Excess ACSF was removed to improve visualization of the brain surface in the pipette lowering stage, and then positive pressure (800-1000 mBar), low positive pressure (25-30 mBar), and suction pressure (−15 to −20 mBar) were applied at the designated ports and the tubing was clamped to the input ports with butterfly clips. The initial state of high positive pressure was present at this time (with all valves electrically off). The 3-axis linear actuator (Siskiyou) was used to manually position the pipette tip over the craniotomy using a control joystick with the aid of a stereomicroscope (Nikon). The pipette was lowered until it just touched the brain surface (indicated by dimpling of surface) and retracted back by 20-30 micrometers. The autopatcher software then denotes this position, just above the brain surface, as z=0 for the purposes of executing the algorithm, acquiring the baseline value R(0) of the pipette resistance at this time (the z-axis is the vertical axis perpendicular to the earth's surface, with greater values going downwards). The pipette voltage offset was automatically nullified by the "pipette offset" function in the Multiclamp Commander (Molecular Devices). It was ensured that electrode wire in the pipette was chlorided enough so as to minimize pipette current drift, which can affect the detection of the small resistance measurements that occur during autopatcher operation. The brain surface was then superfused with ACSF and the autopatcher program was started.

Details of Autopatcher Program Execution. The autopatcher evaluates the pipette electrical resistance is evaluated outside the brain (e.g., between 3-9 MΩ is typical) for 30-60 seconds to see if AgCl pellets or other particulates internally clog the pipette (indicated by increases in resistance). If the pipette resistance remains constant and is of acceptable resistance, the Autopatcher program is started. The program records the resistance of the pipette outside the brain and automatically lowers the pipette to a pre-specified target region within the brain (the "regional pipette localization" 410 stage in FIG. 4), followed by a second critical examination of the pipette resistance for quality control. This check is followed by an iterative process of lowering the pipette by small increments, while looking for a pipette resistance change indicative of proximity to a neuron suitable for recording (the "neuron hunting" stage). During this stage, the robot looks for a specific sequence of resistance changes that indicates that a neuron is proximal, attempting to avoid false positives that would waste time and decrease cell yield. After detecting this signature, the robot halts movement, and begins to actuate suction and pipette voltage changes so as to form a high-quality seal connecting the pipette electrically to the outside of the cell membrane (the "gigaseal formation" stage 430), thus resulting in a gigaseal cell-attached recording. If whole-cell access is desired, the robot can then be used to perform controlled application of suction as well as brief electrical pulses to break into the cell (the "break-in" stage).

Throughout the process, the robot applies a voltage square wave to the pipette (10 Hz, 10 mV alternating with 0 mV relative to pipette holding voltage), and the current is measured, in order to calculate the resistance of the pipette at a given depth or stage of the process. Throughout the entire process of robot operation, this pipette resistance is the chief indicator of pipette quality, cell presence, seal quality, and recording quality, and the algorithm attempts to make decisions—such as whether to advance to the next stage, or to restart a stage, or to halt the process—entirely on the temporal trajectory taken by the pipette resistance during the experiment. The performance of the robot is enabled by two critical abilities of the robot: its ability to monitor the pipette resistance quantitatively over time, and its ability to execute actions in a temporally precise fashion upon the measured pipette resistance reaching quantitative milestones.

Histology and Imaging. For experiments with biocytin filling of cells, mice were perfused through the left cardiac ventricle with ~40 mL of ice-cold 4% paraformaldehyde in phosphate buffered saline (PBS) while anesthetized with isoflurane. Perfused brains were then removed from the skull then postfixed overnight in the same solution at 4° C. The fixed brains were incubated in 30% sucrose solution for 2 days until cryoprotected (i.e., the brains sank). The brains were flash frozen in isopentane cooled using dry ice at temperatures between −30° C. to −40° C. The flash frozen brains were mounted on mounting plates using OCT as base, and covered with tissue embedding matrix to preserve tissue integrity, and 40 μm thick slices were cut at −20° C. using a cryostat (Leica). The brain slices were mounted on charged glass slides (e.g., SuperFrost) and incubated at room temperature for 4 hours in PBS containing 0.5% Triton-X (vol/vol) and 2% goat serum (vol/vol). This was followed by 12-14 hours of incubation at 4° C. in PBS containing 0.5% Triton-X (vol/vol), 2% goat serum (vol/vol) and Alexa 594 conjugated with streptavidin (Life Technologies, diluted 1:200). After incubation, the slices were thoroughly washed in PBS containing 100 mM glycine and 0.5% Triton-X (vol/vol) followed by washing in PBS with 100 mM glycine. Slices were then mounted in Vectashield with DAPI (Vector Labs), covered using a coverslip, and sealed using nail polish. Image stacks were obtained using a confocal microscope (Zeiss) with 20× objective lens. Maximum intensity projections of the image stacks were taken using ImageJ software. If needed to reconstruct full neuron morphology, multiple such maximum intensity projection images were auto-leveled, then montaged, using Photoshop CS5 software.

The present invention provides a methodology, and a robot suited for performing the methodology, for automatically patch clamping cells in the living brain. The invention produces yields, speeds, and quality levels comparable to or exceeding what trained human investigators can perform. The methodology involves precision measurements, including measurements of sequences of pipette electrophysiological events, as well as precision movements, such as being able to halt pipette movements immediately following detection of such events. The methodology also involves temporally precise control of pressure, essential for enabling pipettes to descend to depth and for high-fidelity cell-attached and whole-cell recordings to be obtained. The methodology takes advantage of the power of simple robotic design principles, for example the ability to analyze temporal trajectories of quantitative data (in a fashion that is difficult for humans), and performing fast actuation events triggered by these analyses. Importantly, the finding of the methodology itself would have been difficult without a robotic platform for evaluating systematically the parameters governing the success of in vivo patch clamping. Thus, it is anticipated that other applications of robotics to the automation of complex neuroscience experiments will be possible and facilitated by the realization that a cycle of innovation in which the engineering and science iterate is useful in the discovering and creation of scientifically-impactful technologies.

Some aspects of in vivo patching had been standardized prior to this invention. For example, pipette solutions must have osmolarity and pH defined within strict numerical limits. Most other aspects of patch clamping, however, have been regarded as human skills requiring dynamic evaluation of situations and adaptation to complex in vivo events. The present invention demonstrates that the decisions to be made, and the measurements and analyses leading to these decisions, can be codified in algorithmic form. With a single set of thresholds of detection, protocols for achieving seals, and criteria for gauging the progress from one stage of the patch process to another, it was possible to record cells in both the hippocampus and the cortex (despite the algorithm having been derived from cortical experiments alone), implying a degree of generality to the methodology of the invention. For cells that are vastly different from cells of the hippocampus and cortex, e.g. cerebellar granule cells whose small size requires high resistance pipettes, or cells in non-brain structures or in other species such as Drosophila, it is likely that the precise parameters utilized might need to be adjusted. The iterative process utilized to derive the algorithm above, however, is in part automated by the existence of the robot—for example, the robot may be able to track yields and adaptively modify parameters if the recordings are failing at too high a rate. The robot automates the process, reducing the cost of iteration, as well as the skill required to iterate, thus opening up the methodology itself to a broader population.

The present invention may open up many new frontiers in biology, bioengineering, and medicine in which the assessment of the properties of single cells, embedded within intact tissue, is desired but has not been achievable in a systematic high-throughput fashion. For example, analyzing how different cells in a neural circuit respond to a drug in specific brain states, performing electrical characterizations of cells in tissues removed during surgery, determining how different individual cells within a tumor biopsy sample vary in gene expression, and assessing how tissue-engineered organs vary in cell to cell composition, may provide fundamental new capabilities in diagnostics, personalized medicine, and drug development. The ability to determine whether a recorded cell is of a given cell class, using optical activation of specific cells within that class as a way of indicating the identity of those cells, would be aided by the ability to rapidly patch cells, thus enabling optogenetic cell identification. The autopatcher robot's pipette can potentially be integrated with capillary systems for liquid chromatography and mass spectrometry for single cell proteomic analysis. Automation both speeds up processes and reduces the skill levels required, enabling for example a single robot operator to control many rigs; these effects will greatly broaden the number of fields for which single-cell analyses in intact tissue are applicable.

The apparatus of the present invention is based on a relatively inexpensive modification to a conventional patch rig, and thus can easily be incorporated into existing labs' setups. Such a rig is capable of enabling the recording of many dozens of cells per experiment in an automated fashion, but higher throughput devices and devices with new features would expand the power of this robotic approach even further. For example, given that only a single linear drive is required, a head borne version for freely moving animals (e.g., building off the protocols described by Lee. A. K. et al., Whole-cell recordings in freely moving rats, Neuron 51, 399-407 (2006)]) might be easily achieved. Image-guided versions may be developable, which use microscopy to identify targets, but then use the autopatcher algorithm to detect the cell membrane, obtain the seals, and achieve whole-cell access. The ability to automatically make micropipettes in a high-throughput fashion, and to install them automatically, might eliminate some of the few remaining steps requiring human intervention. As a final example, the ability to actuate many pipettes within a single brain, and to perform massively recordings of neurons or other cells within a single living network, may open up the ability to analyze neural computations and other biological phenomena with great accuracy. The algorithmic nature of the procedure described here, and the simple robotics needed to implement it, not only open up many kinds of scientific investigation, but also empower new kinds of neuroengineering to be contemplated and pursued.

While a preferred embodiment is disclosed, many other implementations will occur to one of ordinary skill in the art and are all within the scope of the invention. Each of the various embodiments described above may be combined with other described embodiments in order to provide multiple features. Furthermore, while the foregoing describes a number of separate embodiments of the apparatus and method of the present invention, what has been described herein is merely illustrative of the application of the principles of the present invention. Other arrangements, methods, modifications, and substitutions by one of ordinary skill in the art are therefore also considered to be within the scope of the present invention, which is not to be limited except by the claims that follow.

What is claimed is:

1. A method for automated whole-cell patch clamping, comprising the steps of:
   regionally localizing a recording electrode of a cell patch clamping device, the recording electrode having a tip, by causing the tip of the recording electrode to be lowered to a predetermined depth for neuron hunting;
   iteratively lowering the tip of the recording electrode by a pre-set amount;
   measuring the resistance at the recording electrode tip after each iteration of the step of lowering;
   determining whether or not a target neuron has been encountered by constructing a temporal series of the resistance measurements after each iteration of the steps of lowering and measuring;

iteratively continuing the steps of lowering, measuring, and determining until the temporal series of resistance measurements indicates monotonic increases in resistance over a threshold number of consecutive iterations and the increase in resistance over the measured temporal series is above a pre-set neuron detection threshold;

stopping the iterative lowering of the recording electrode;

initiating gigaseal formation;

assessing whether or not gigaseal formation has been achieved;

if gigaseal formation has been achieved, initiating break-in and formation of a whole-cell patch clamp; and verifying formation of the whole-cell patch clamp.

2. The method of claim 1, further comprising the step of forming a gigaseal-attached patch after gigaseal formation has been achieved and verified.

3. The method of claim 1, further comprising the step of providing positive pressure to the cell patch clamping device during the step of regionally localizing.

4. The method of claim 3, further comprising the steps of:
after completing the step of regionally localizing,
reducing the pressure provided to the cell patch clamping device to low positive pressure;
measuring the resistance at the recording electrode tip;
assessing whether or not the measured resistance has increased over a pre-set tip blockage threshold; and
if the measured resistance has increased over the tip blockage threshold, retracting the cell patch clamping device to indicate tip blockage and failure.

5. The method of claim 4, wherein the step of initiating gigaseal formation further comprises the step of releasing the positive pressure applied to the cell patch clamping device.

6. The method of claim 5, further comprising the steps of:
after the step of assessing, if gigaseal formation has not been achieved, applying suction pressure to the cell patch clamping device; and
re-assessing whether or not gigaseal formation has been achieved.

7. The method of claim 6, wherein the step of initiating break-in and formation further comprises applying at least one of suction and an electrical pulse to the cell patch clamping device.

8. The method of claim 1, further comprising the step of:
if a predetermined maximum level for lowering the electrode tip has been reached, retracting the cell patch clamping device to indicate neuron location failure.

9. A method for achieving and verifying neuron contact in an automated electrophysiology device, comprising the steps of:
regionally localizing a recording electrode of an automated electrophysiology apparatus, the recording electrode having a tip, by causing the tip of the recording electrode to be lowered to a predetermined depth for neuron hunting;
iteratively lowering the tip of the recording electrode by a pre-set amount;
measuring the resistance at the recording electrode tip after each iteration of the step of lowering;
determining whether or not a target neuron has been encountered by constructing a temporal series of the resistance measurements after each iteration of the steps of lowering and measuring; and
iteratively continuing the steps of lowering, measuring, and determining until the temporal series of resistance measurements indicates monotonic increases in resistance over a threshold number of consecutive iterations and the increase in resistance over the measured temporal series is above a pre-set neuron detection threshold that indicates that neuron contact has been achieved.

10. An apparatus for automated cell patch clamping, comprising:
a cell patch formation apparatus, comprising:
at least one cell patch clamping device having a recording electrode, the recording electrode having a tip;
a clamping device-positioning 3-axis linear actuator connected to the cell patch clamping device; and
a patch amplifier with computer interface;
a clamping device-moving programmable linear motor connected to the 3-axis linear actuator in a manner permitting moving the cell patch clamping device up and down;
a resistance monitoring mechanism; and
a computer interface configured for automated closed-loop control of the programmable motor based upon a temporal series of resistance measurements at the tip of the recording electrode.

11. The apparatus of claim 10, further comprising an automated control system configured for:
causing the tip of the recording electrode to be lowered to a predetermined depth for neuron hunting;
iteratively causing the tip of the recording electrode to be lowered by a pre-set amount;
measuring the resistance at the recording electrode tip after each iteration of the step of lowering;
determining whether or not a target neuron has been encountered by constructing a temporal series of the resistance measurements after each iteration of the steps of lowering and measuring;
iteratively continuing the steps of lowering, measuring, and determining until the temporal series of resistance measurements indicates monotonic increases in resistance over a threshold number of consecutive iterations and the increase in resistance over the measured temporal series is above a pre-set neuron detection threshold;
stopping the iterative lowering of the recording electrode;
initiating gigaseal formation;
assessing whether or not gigaseal formation has been achieved;
if gigaseal formation has been achieved, initiating break-in and formation of a whole-cell patch clamp; and
verifying formation of the whole-cell patch clamp.

12. The apparatus of claim 11, wherein the automated control system is further configured for causing formation of a gigaseal-attached patch after gigaseal formation has been achieved and verified.

13. The apparatus of claim 11, further comprising a controllable plurality of pneumatic valves configured for application of pressure and suction to the cell patch clamping device.

14. The apparatus of claim 13, wherein the controllable plurality of pneumatic valves is configured for providing positive pressure to the cell patch clamping device while the tip of the recording electrode is lowered to the predetermined depth for neuron hunting.

15. The apparatus of claim 14, wherein the controllable plurality of pneumatic valves is configured for reducing the pressure provided to the cell patch clamping device to low positive pressure after the tip of the recording electrode has been lowered to the predetermined depth for neuron hunting; and the automated control system is further configured for:
  measuring the resistance at the recording electrode tip;
  assessing whether or not the measured resistance has increased over a pre-set tip blockage threshold; and
  if the measured resistance has increased over the tip blockage threshold, directing the linear motor to retract the cell patch clamping device to indicate tip blockage and failure.

16. The apparatus of claim 15, wherein the controllable plurality of pneumatic valves is further configured for releasing the positive pressure applied to the cell patch clamping device during initiation of gigaseal formation.

17. The apparatus of claim 16, wherein the controllable plurality of pneumatic valves is further configured for applying suction pressure to the cell patch clamping device if gigaseal formation has not been achieved.

18. The apparatus of claim 16, wherein the controllable plurality of pneumatic valves further comprises applies at least one of suction and an electrical pulse to the cell patch clamping device to initiate break-in and whole-cell patch clamp formation.

19. A method for controlling an automated cell patch clamping device, comprising the steps of:
  in a cell patch formation apparatus, comprising:
    at least one cell patch clamping device having a recording electrode, the recording electrode having a tip;
    a clamping device-positioning 3-axis linear actuator;
    a patch amplifier with computer interface;
    a clamping device-moving programmable linear motor; and
    a computer interface configured for closed-loop control of the programmable motor based upon sequences of resistance measurements made at the tip of the recording electrode,
  regionally localizing the recording electrode by causing the linear motor to lower the tip of the recording electrode to a predetermined depth for neuron hunting;
  causing the linear motor to iteratively lower the tip of the recording electrode by a pre-set amount;
  measuring the resistance at the recording electrode tip after each iteration of the step of lowering;
  determining whether or not a target neuron has been encountered by constructing a temporal series of the resistance measurements after each iteration of the steps of lowering and measuring;
  iteratively continuing the steps of lowering, measuring, and determining until the temporal series of resistance measurements indicates monotonic increases in resistance over a threshold number of consecutive iterations and the increase in resistance over the measured temporal series is above a pre-set neuron detection threshold;
  causing the linear motor to stop the iterative lowering of the recording electrode;
  initiating gigaseal formation;
  assessing whether or not gigaseal formation has been achieved;
  if gigaseal formation has been achieved, initiating break-in and formation of a whole-cell patch clamp; and
  verifying formation of the whole-cell patch clamp.

20. The method of claim 19, wherein the cell patch formation apparatus further comprises a controllable plurality of pneumatic valves configured for application of pressure and suction to the cell patch clamping device and further comprising the steps of:
  providing positive pressure from the controllable plurality of pneumatic valves to the cell patch clamping device during the step of regionally localizing;
  after completing the step of regionally localizing,
    reducing the pressure provided to the cell patch clamping device to low positive pressure;
    measuring the resistance at the recording electrode tip;
    assessing whether or not the measured resistance has increased over a pre-set tip blockage threshold; and
    if the measured resistance has increased over the tip blockage threshold, retracting the cell patch clamping device to indicate tip blockage and failure;
  wherein the step of initiating gigaseal formation further comprises releasing the positive pressure applied to the cell patch clamping device;
  after the step of assessing, if gigaseal formation has not been achieved,
    applying suction pressure from the controllable plurality of pneumatic valves to the cell patch clamping device; and
    re-assessing whether or not gigaseal formation has been achieved; and
  wherein the step of initiating break-in and formation further comprises applying to the cell patch clamping device at least one of: suction pressure from the controllable plurality of pneumatic valves and an electrical pulse.

* * * * *